(12) United States Patent
Costantino

(10) Patent No.: US 12,381,001 B2
(45) Date of Patent: *Aug. 5, 2025

(54) SECURE SYSTEMS FOR CONTACTLESS IDENTIFICATION AND VITAL SIGN MONITORING

(71) Applicant: AION Biosystem, Inc., Darien, CT (US)

(72) Inventor: Peter Costantino, Westport, CT (US)

( * ) Notice: Subject to any disclaimer, the term of this patent is extended or adjusted under 35 U.S.C. 154(b) by 533 days.

This patent is subject to a terminal disclaimer.

(21) Appl. No.: 17/588,141

(22) Filed: Jan. 28, 2022

(65) Prior Publication Data

US 2022/0148726 A1 May 12, 2022

Related U.S. Application Data

(63) Continuation of application No. 16/907,134, filed on Jun. 19, 2020, now Pat. No. 11,309,083, which is a
(Continued)

(51) Int. Cl.
*A61B 5/00* (2006.01)
*A61B 5/0205* (2006.01)
(Continued)

(52) U.S. Cl.
CPC ........... *G16H 40/67* (2018.01); *A61B 5/0022* (2013.01); *A61B 5/0205* (2013.01);
(Continued)

(58) Field of Classification Search
CPC ........ G16H 40/67; G16H 50/80; G16H 40/20; A61B 5/0205; A61B 5/6833; A61B 90/90;
(Continued)

(56) References Cited

U.S. PATENT DOCUMENTS 11,309,083 B2 * 4/2022 Costantino ......... G06Q 30/0185

* cited by examiner

*Primary Examiner* — Christle I Marshall
(74) *Attorney, Agent, or Firm* — Handal & Morofsky LLC; Anthony H. Handal

(57) ABSTRACT

A system for identifying, monitoring the health of an individual and providing for the retrieval of information relating to said individual by a plurality of authorized users. The system comprises an identification device and associated hardware and software components. The identification device a skin wearable, waterproof, non-transferable frangible individual identification device comprising (1) an adhesive and marking arranged on a substrate to provide a physiologically perceptible, humanly understandable information related to said individual, and (2) an electronic device having wireless communication capability with the ability to send, receive, and store information, wherein electronic device comprises at least one sensor for taking vital sign data, wherein once applied to skin, removal of the individual renders the identification device inoperable wherein the marking, substrate, and adhesive are biocompatible. The associated hardware includes a plurality of receivers; a computer interface device receiving information from said individual identification device and from said receivers respecting the individual identified by said individual identification device; a computer system coupled to said computer interface device, said computer system including a memory with an algorithm for processing information collected by said computer system; and a separate set of receivers and a separate service rendering system, each output information from their respective receivers to a common database, the contents of said common database being coupled to a computing device which communicates information to and from a central server. In a preferred embodiment, the identification device is a Bluetooth compatible, battery powered, identification and monitoring (Continued)

device measuring temperature, pulse oximetry and heart rate.

25 Claims, 16 Drawing Sheets

Related U.S. Application Data continuation-in-part of application No. 16/896,184, filed on Jun. 8, 2020, now Pat. No. 11,217,348, which is a continuation-in-part of application No. 16/721,389, filed on Dec. 19, 2019, now Pat. No. 11,056,245, which is a continuation-in-part of application No. 16/140,080, filed on Sep. 24, 2018, now Pat. No. 10,810,479, which is a continuation-in-part of application No. 15/699,427, filed on Sep. 8, 2017, now Pat. No. 10,083,391, which is a continuation-in-part of application No. 15/295,144, filed on Oct. 17, 2016, now Pat. No. 9,996,789, which is a continuation-in-part of application No. 14/862,081, filed on Sep. 22, 2015, now abandoned, and a continuation-in-part of application No. 14/862,033, filed on Sep. 22, 2015, now Pat. No. 9,519,724, and a continuation-in-part of application No. 14/860,646, filed on Sep. 21, 2015, now Pat. No. 9,489,466.

(60) Provisional application No. 63/026,368, filed on May 18, 2020, provisional application No. 62/882,094, filed on Aug. 2, 2019, provisional application No. 62/880,262, filed on Jul. 30, 2019, provisional application No. 62/875,684, filed on Jul. 18, 2019, provisional application No. 62/825,514, filed on Mar. 28, 2019, provisional application No. 62/793,293, filed on Jan. 16, 2019, provisional application No. 62/690,413, filed on Jun. 27, 2018, provisional application No. 62/690,341, filed on Jun. 26, 2018, provisional application No. 62/618,782, filed on Jan. 18, 2018, provisional application No. 62/580,952, filed on Nov. 2, 2017, provisional application No. 62/531,863, filed on Jul. 12, 2017, provisional application No. 62/500,419, filed on May 2, 2017, provisional application No. 62/426,765, filed on Nov. 28, 2016, provisional application No. 62/377,786, filed on Aug. 22, 2016, provisional application No. 62/375,892, filed on Aug. 16, 2016, provisional application No. 62/365,988, filed on Jul. 23, 2016, provisional application No. 62/359,104, filed on Jul. 6, 2016, provisional application No. 62/357,240, filed on Jun. 30, 2016, provisional application No. 62/242,973, filed on Oct. 16, 2015, provisional application No. 62/053,725, filed on Sep. 22, 2014.

(51) Int. Cl.
| | | |
|---|---|---|
| *A61B 90/90* | (2016.01) | |
| *A61B 90/98* | (2016.01) | |
| *G06F 21/44* | (2013.01) | |
| *G06K 7/14* | (2006.01) | |
| *G06Q 30/018* | (2023.01) | |
| *G06Q 50/26* | (2012.01) | |
| *G16H 10/65* | (2018.01) | |
| *G16H 40/67* | (2018.01) | |
| *G16H 50/30* | (2018.01) | |
| *H04W 4/029* | (2018.01) | |
| *H04W 4/38* | (2018.01) | |
| *H04W 4/80* | (2018.01) | |
| *A61B 5/024* | (2006.01) | |
| *A61B 5/11* | (2006.01) | |
| *A61B 5/1455* | (2006.01) | |
| *A61B 90/96* | (2016.01) | |
| *G16H 50/80* | (2018.01) | |

(52) U.S. Cl.
CPC ............ *A61B 5/6833* (2013.01); *A61B 90/90* (2016.02); *G06F 21/44* (2013.01); *G06K 7/1417* (2013.01); *G06Q 30/0185* (2013.01); *G06Q 50/265* (2013.01); *G16H 10/65* (2018.01); *G16H 50/30* (2018.01); *H04W 4/029* (2018.02); *H04W 4/38* (2018.02); *H04W 4/80* (2018.02); *A61B 5/02438* (2013.01); *A61B 5/1112* (2013.01); *A61B 5/14551* (2013.01); *A61B 90/96* (2016.02); *A61B 90/98* (2016.02); *A61B 2562/166* (2013.01); *A61B 2562/18* (2013.01); *G16H 50/80* (2018.01)

(58) Field of Classification Search
CPC ... A61B 5/02438; A61B 90/98; H04W 4/029; H04W 4/38; H04W 4/80; G06F 21/35; G09F 3/0292
See application file for complete search history.

SECURE SYSTEMS FOR CONTACTLESS IDENTIFICATION AND VITAL SIGN MONITORING

CROSS REFERENCE TO RELATED APPLICATIONS

This application is a continuation of U.S. patent application Ser. No. 15/699,427 Visually, Optically and electronically Readable Frangible Device for Affixation to the Skin filed Sep. 8, 2017 and continuation-in-part of International Application No. PCT/US2015/051289, entitled, Security and Accounting Infrastructure, and Associated Cutaneous Information Device and Method, filed on Sep. 22, 2015, which claims priority to U.S. Provisional Application No. 62/053,725, entitled, Temporary Cutaneous Information Device and Associated Method and Multi-Patient Treatment Infrastructure, filed on Sep. 22, 2014. This application also claims priority of International Application PCT/US2017/048085, entitled, Improved Visually, Optically and Electronically Readable Frangible Device for Affixation to the Skin, filed on Aug. 22, 2017, as well as applications International Application PCT/US2017/040053 System and Method for Transitions of Care, filed Jun. 29, 2017, U.S. patent application Ser. No. 14/860,646, Transportation and Resort Infrastructure, and Associated Cutaneous Information Device and Method, filed Sep. 21, 2015, U.S. patent application Ser. No. 14/862,033, Temporary Cutaneous Information Device and Associated Method and Multi-Patient Treatment Infrastructure and U.S. patent application Ser. No. 14/862,081 Temporary Cutaneous Information Device, Associated Method and Resort Infrastructure both filed on Sep. 22, 2015, U.S. Provisional Patent Application No. 62/242,973 Method and Apparatus for Manufacturing Cutaneous Information Devices, filed Oct. 16, 2015, U.S. Provisional Application No. 62/357,240 Transitions of Care Information Device, filed on Jun. 30, 2016, U.S. Provisional Application No. 62/359,104 Skin Applied Point of Service Preparation Device Process and Design Technical Field, filed on Jul. 6, 2016, U.S. Provisional Application No. 62/365,988 Method for the Biocompatible Skin Safe Application of Multiple Color Images to the Skin filed Jul. 23, 2016, U.S. Provisional Application No. 62/375,892 Method For Biocompatible Skin Safe Application of One or More Color Images To the Skin Using Sublimation Printing, filed Aug. 16, 2016, U.S. Provisional Patent Application No. 62/377,786 entitled Improved Visually, Optically and Electronically Readable Device for Durable Affixation to the Skin filed on Aug. 22, 2016, U.S. patent application Ser. No. 15/295,144 Method and Apparatus for Manufacturing Cutaneous Information Devices, filed Oct. 17, 2016, U.S. Provisional Patent Application No. 62/426,765 Method For Biocompatible Skin Safe Application of One or More Color Images To The Skin Using Thermal Printing, filed on Nov. 28, 2016, U.S. Provisional Patent Application No. 62/500,419 Construct Design and Application of Cutaneous Information Device for Enhanced Physical Authentication Including a Streamlined Digital Authentication Process, filed May 2, 2017, U.S. Provisional Patent Application No. 62/531,863 Nontransferable Identification Device, filed Jul. 12, 2017. additionally, priority is claimed to U.S. Provisional Patent Application No. 62/580,952 Customizable Cutaneous Information Devices and Manufacturing Methods for the Same filed Nov. 2, 2017, and U.S. Provisional Patent Application No. 62/618,782 Cost Effective Cutaneous Information Devices With Enhanced Frangibility filed Jan. 18, 2018, U.S. Provisional Patent Application No. 62/690,341, Enhanced Cutaneous Information Device With Proximity Detection filed Jun. 26, 2018, U.S. Provisional Patent Application No. 62/690,413 Cutaneous Information Device System with Wireless Detection of Patron Location filed on Jun. 27, 2018, U. S. Provisional Patent Application No. 62/793,293 Improvements To Cutaneous Information Device Structure filed on Jan. 16, 2019, U.S. Provisional Patent Application No. 62/825,514 Cutaneous Smart Tag With Redundant Electronic/Visual Security Mechanism filed on Mar. 28, 2019, U.S. Provisional Patent Application No. 62/875,684 entitled Systems For Point of Service Customization and Printing of Non Transferable Cutaneous Identification Devices Using Thermal Transfer Printing filed on Jul. 18, 2019, U.S. Provisional Patent Application No. 62/880,262 entitled Systems for Secure Identification Using Cutaneous Smart Tags with Redundant Electronic/Visual Security Mechanisms filed on Jul. 30, 2019, U.S. Provisional Patent Application No. 62/882,094 entitled Systems and Methods for Transitions of Care filed on Aug. 2, 2019, U.S. Non-provisional patent application Ser. No. 16/721,389 entitled Systems and Methods for Transitions of Care filed on Dec. 19, 2019, U.S. Provisional Patent Application No. 63/026,368 entitled Cutaneous Smart Tag with Biometric Sensor Extending Arm filed on May 18, 2020, U.S. Non-provisional patent application Ser. No. 16/896,184 entitled Systems for Secure Contactless Identification and Tracking with Redundant Electronic/Visual Security Mechanisms filed on Jun. 8, 2020, U.S. Non-provisional patent application Ser. No. 16/907,134 entitled Systems for Secure Contactless Identification and Tracking in the Field with Redundant Electronic/Visual Security Mechanisms filed on Jun. 19, 2020, the disclosures of all of the above are incorporated herein by reference.

TECHNICAL FIELD

The invention relates to Cutaneous Information Devices (CID) skin worn devices for purpose of identification, data collection, electronic systems integration, physiologic and other skin applied sensing and delivery of dynamic, unique, authenticated and secure content allowing both interface with information technology infrastructure and direct to human information communication in a structure which provides independent and redundant human and machine-readable indications of tampering, particularly useful for providing a secure and reliable method of identification and tracking of an individual.

BACKGROUND

Identification has long been a feature of numerous consumer and commercial systems ranging from such things as driver identification, admission to secure facilities such as airports and hospitals, and so forth.

Nevertheless, notwithstanding very significant advances in many sectors of the healthcare and other industries, the inability to quickly identify patients, for example, accurately and durably, continues to result in numerous incidents. Consequences may include medication errors, transfusion errors, medication errors, mistaken phlebotomies, surgery errors, financial and other issues, testing errors, wrong person procedures, and the discharge of infants to the wrong families. Numerous incidents are reported every year with patient misidentification cited in individual root cause analyses, such as that conducted by the United States Department of Veterans Affairs (VA) National Center for Patient Safety. Nevertheless, despite availability of numerous products and strategies designed to reduce the risk of patient misidentification and the consequences of such incidents, the problem persists.

Moreover, continuing pressure to limit hospital staff working hours increases the risk of such errors, due to the increased number of staff nurses, technicians, residents and other doctors caring for each patient. Thus, hand-over and other communication risks are increased as current medical care strategies evolve. Further during acute medical crises such as a pandemic, the system is further strained with a large influx of patients, some of whom cannot talk or who lose the ability to communicate accurately or coherently while they are at the hospital.

Current methodology for the identification of patients at medical facilities generally involves the use of a wrist bracelet. Problems with current band methods of identification include interference with intravenous insertion, the need to remove during certain procedures situations, the fact that such bands are uncomfortable, and the possibility of their presenting a hazard. Such bands also carry limited information, sometimes making necessary additional devices. Given the longstanding high-profile recognition that patient misidentification is a serious problem, numerous but ineffective solutions have been proposed, including barcoding, color coding of patient wristbands, use of multiple identification strategies, and venous pattern recognition systems.

However, despite the availability of such a wide range of tagging and identification systems, and despite their drawbacks and limitations, simple alphanumeric patient identification wristbands remain the only significant method employed for identification of patients. Other tagging and identification systems face significant obstacles to implementation in the context of a multi-patient medical facility. Barcoding schemes require significant and expensive hardware at the point of care. Moreover, in critical situations, the absence of immediate availability of barcode reading equipment can result in unacceptable delay.

Thus, despite all their problems, as noted above, and even the potential of providing a choking hazard to newborns, nevertheless, patient wristbands including only a minimal amount of information remain, by an overwhelming majority, the dominant patient identification system currently in use.

Identification devices are useful in other areas where identification is a value for various reasons, such as security, payments, and so forth. More particularly, resorts, country clubs, municipal recreational facilities, cruise ships, convention centers, theme parks, museums and so forth often have many recreational options which are made available to large numbers of people. Such options may include theatrical presentations, rides, restaurants, fast food facilities, classes, parties, meetings, exhibition halls, pools, tennis courts, horseback riding, and so forth. Operators of such facilities often have a number of reasons for controlling and/or monitoring use of and or access to their facilities, and the various attractions located therein by patrons.

At the present time, in a typical facility, one or more individuals are present at the entrance to the venue hosting the attraction, event or other offering. These individuals check persons wishing to enter the attraction venue, requesting and/or collecting and/or ripping tickets in half.

Tickets to facilities, such as amusement parks, are often purchased on the Internet. However, due to the fact that multiple tickets can be printed, consumers are generally provided only with an identification number or alphanumeric. When the individual arrives at the attraction, he or she presents the reservation number at a kiosk where specially printed tickets are provided. Typically, these tickets are collected and ripped in half at the venue. These specially printed tickets have a format which is largely unknown to the individual attending and offering and which may be difficult to copy.

Such systems suffer from multiple drawbacks. For example, the cost of personnel at the entrance to the venue is high. Moreover, for quality of service reasons, multiple personnel are often employed at the entrance to the venue. In addition, the possibility exists that reservations may be made and resold by "scalpers". Individuals may even swap tickets once they enter the facility, posing a security risk.

The largest drawback of any system which involves the exchange of any sort of physical ticket is the potential to spread germs. Under the conditions of a health crisis, such as a pandemic or even during a bad flu season, exchanging tickets would no longer be feasible as facilities want to avoid the spread of germs at public events.

It is also desirable to track usage at a facility and for many years numerous solutions have been proposed and implemented. For example, using a rubber stamp and printed layer to identify individuals who have paid a fee is something which has been done for at least 50 years. However, given the desire to avoid germs, it is no longer reasonable to use a rubber stamp. It would also be desirable not just to track usage at a facility while they are there, but also track physical proximity to other guests at the facility for potential future contact tracing.

The need for accurate individual identification across all settings including home, business, recreation and medical settings becomes all the more acute with the onset of an epidemic. Given an epidemic where people may be asymptomatic, contact tracing is highly desirable and presently difficult to manage due to the lack of accuracy in identification of individuals.

Despite their drawbacks and limitations, wristbands, tickets and rubberstamps applied to the skin of the user remain the only significant methodologies used for identification and tracking of individuals in medical and commercial facilities. Given the future acute need to limit physical contact to help stop the spread of disease, there is a need for a secure, contactless identification system that can be used across multiple settings.

SUMMARY OF INVENTION

A system for secure contactless identification and tracking with redundant electronic/visual security mechanisms is provided.

In accordance with the invention, a secure cutaneous identification device (CID) is provided which addresses the above needs in the context of providing human readable information, machine-readable information and an interface to digital infrastructure while minimizing the need for physical contact. The device would be securely paired with the individual wearer. In preferred embodiments, tampering would be prevented through electronic monitoring and the measurement of biometrics of the wearer.

The system's CID is non-transferable, frangible, and also comprises a near field communication device (Bluetooth, RFID, etc. . . . ) where the CID is first authenticated with a smart device post identification verification and security check and affixed to the individual and once there is entry, there is constant monitoring of the CIDs in the venue.

In preferred embodiments, the system would comprise a skin wearable, waterproof, non-transferable frangible individual identification device comprising an adhesive and a marking arranged to provide a physiologically perceptible, humanly understandable, and machine readable information relating to said individual; said identification device is effectively tactically imperceptible and comprises an adhesive layer and a marking containing individual specific information which can be visually seen, read or scanned for patient identification, interaction, information exchange, and instructions and a non-contact communication device; in combination with a plurality of reader devices; a computer interface device receiving information from said individual identification device and from said reader devices respecting the individual identified by said individual identification device; a computer system coupled to said computer interface device, said computer system including a memory with an algorithm for processing information collected by said computer system; and comprising a separate set of reader devices and a separate service rendering system, each output information from their respective reader devices to a common database, the contents of said common database being coupled to a computing device which communicates information to and from a central server.

In a commercial setting, the system may be used to 1) verify the identity of the patron and security clearance; 2) once the tickets are purchased the CID is preprinted and mailed to the patron with a specific CID which confirms identity using a photograph on the CID; and 3) entry into the event, security clearance, overall location or seat number and any other pertinent information to the event, thereby offering no hassle access to venue or event with all pertinent information accessed from the CID, including a photo of the seat, the seat number, section, etc. In a preferred embodiment, the software would also have facial recognition capability to confirm the user's identity. In some embodiments, a scannable code is included for an extra layer of security.

In a medical setting, the system may be used to 1) verify the identity of the patient with a CID 2) track inpatient care 3) track outpatient care and provide contact tracing. In preferred embodiments, the software would also have facial recognition to confirm that the user's face matches the face printed on the CID. In some embodiments, a QR code is included for easier scanning or an extra layer of security. In other embodiments, there would be no facial recognition but confirmation of identity through other biometric measurements.

A noncontact communication device such as RFID or Bluetooth technology can be added. The RFID can consist of both UHF and NFC technology on the same chip, although UHF cannot currently be used on the skin without creating a barrier between the body and the antenna. In a preferred embodiment, the device will have functioning UHF and NFC technology. RFID technology can also include sensing technology.

Temperature measurement is a key measure for infectious diseases as the onset of infection from compromised immune systems, as in oncology patients, the flu, for other viruses such as Covid 19. Treating an infectious disease early reduces hospital admissions, and in particular to which manner of care the patient receives, (patient room, vs. critical care vs. full isolation).

In a preferred embodiment, the device can be used on outpatient and inpatient hospital populations. In a preferred embodiment, sensors will measure temperature on the chest and will transmit body temperature via a Bluetooth connection to a mobile device, or gateway device connected to the Internet. Once received by the cloud services, the data is transmitted to a clinician portal for diagnosis and action if necessary. In a preferred embodiment, there would be sensors to measure for Pulse Oximetry, heart rate, fall detection, and body position. The device would also transmit a signal (e.g., RSSI signal) such that in a hospital equipped with Real Time Location Services (RTLS); the location of the patient can be achieved. The associated LTE gateways combined with NFC capability allows pairing the devices such as weight scales, and blood pressure monitors, devices for EKG measurement.

Sensors may also be incorporated into the device to measure other biometric factors including but not limited to motion, body position, weight, blood pressure, heartrate, cardiac function including but not limited to EKG, blood chemistry such as but not limited to glucose, or any other physiologic signals or sampled quantitated values. This is particularly advantageous for not only telehealth but also remote monitoring. For example, some COVID-19 patients have silent hypoxia where they are alert and feel relatively well yet have remarkably low blood oxygen saturation levels which can lead to death. By the time, they make it to the hospital, the lack of symptoms can make triage extremely difficult. Thus, it would be advantageous for a hospital to be able to scan patient CIDs to properly triage. In preferred embodiments, the CID would include Bluetooth capability, be battery powered, be useful as an identification and monitoring device to measure vital signs such as pulse oximetry and heart rate to alert authorities to health distress in the field. In an alternative embodiment where there is no RFID reader, a visual code may be scanned to remotely confirm identity.

The system is different from any existing personal identification and monitoring system as it is securely united to the person's identity and cannot be separated from the person once authenticated. Security can be assured through a number of means including sensors, markings, NFC tags, biorhythm profiles.

BRIEF DESCRIPTION OF THE FIGURES

A more complete understanding of the present invention and the advantages thereof may be acquired by referring to the following description in consideration of the accompanying drawings, in which like reference numbers indicate like features, and wherein.

DETAILED DESCRIPTION OF INVENTION

Generally, in accordance with the invention, the inventive method (described in detail below) is initiated by a person entering a facility and providing identifying information. The information is communicated to a central database/processor directly or via a local server/processor through, for example, a plurality of Internet connected computers, or, as illustrated, cellular smart devices (such as smartphones). Cellular smart devices are connected, via cell towers and cyberspace to a central server. The information is checked to verify if the person is already registered in the system or if a new record needs to be created. Then the secure CID is applied to the surface of the skin. The CID in connection with authorized devices will be used to verify the identity of this individual. Access to the information contained on the central server will be managed by security protocols to ensure that the information being provided is on a need to know basis.

Figure 1:
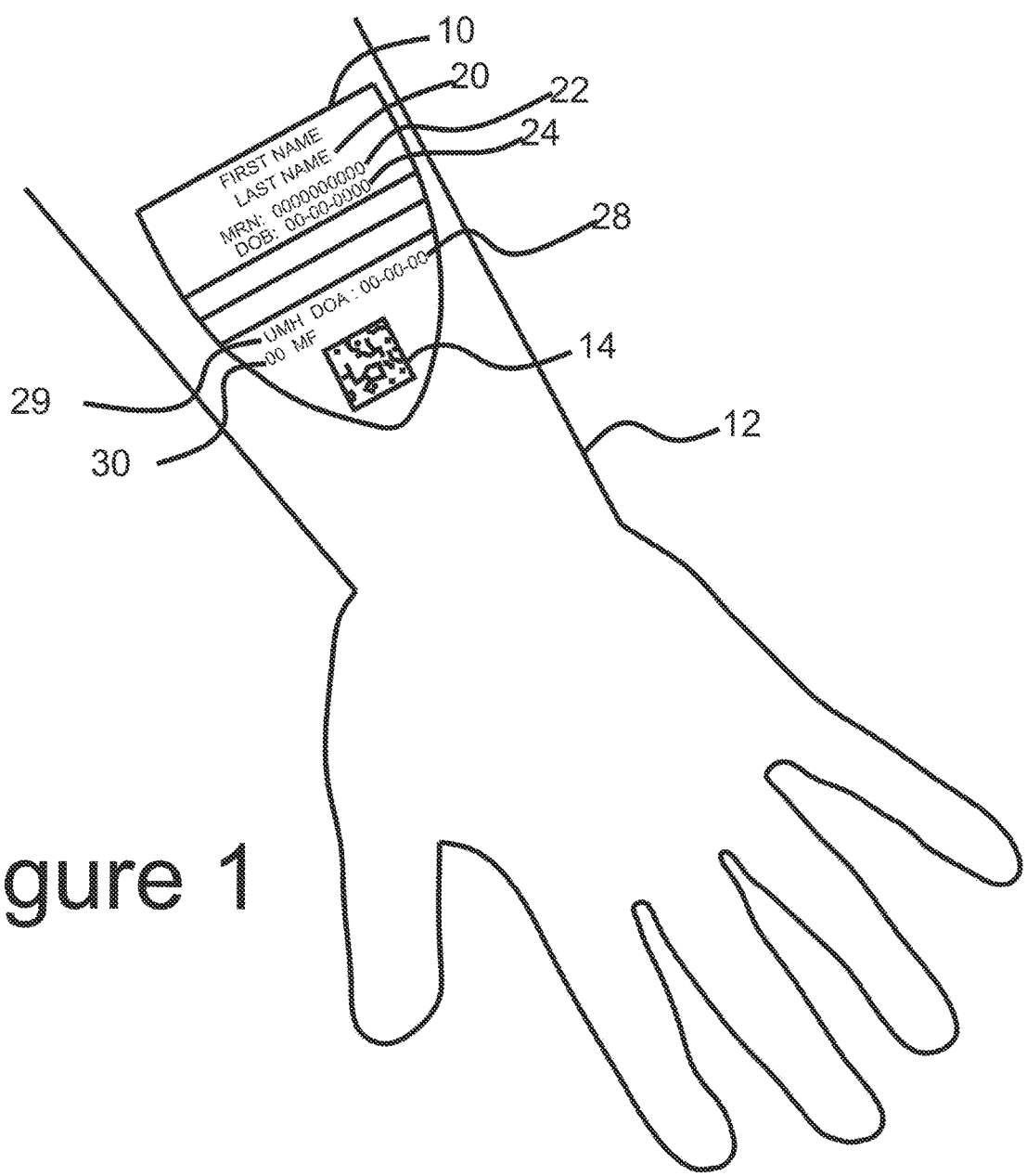
FIG. 1 shows a preferred embodiment of the CID applied to a surface of the skin with detail on the visually displayed information located on the CID including an optically read code, which in this example is a datamatrix code.

FIG. 1 shows a preferred embodiment of a CID applied to a surface of the skin with detail on the visually displayed information located on the CID including an optically read code, which in this example is a datamatrix code. CID 10 comprises adhesive and a marking would be on the substrate at the point of service. CID 10 is applied to an individual's forearm 12. In accordance with the invention, it is contemplated that different sized CIDs may be used for larger and smaller people as well as varying application locations for the CID based on the environment. In a preferred embodiment, CID 10 would be effectively tactically imperceptible so that it would not bother the wearer. Upon arrival to the origination point, the individual is identified using CID 10 embedded with a two-dimensional code 14 such as a QR or data matrix code, other optical code system and/or an RFID chip or other noncontact communication device.

Figure 2:
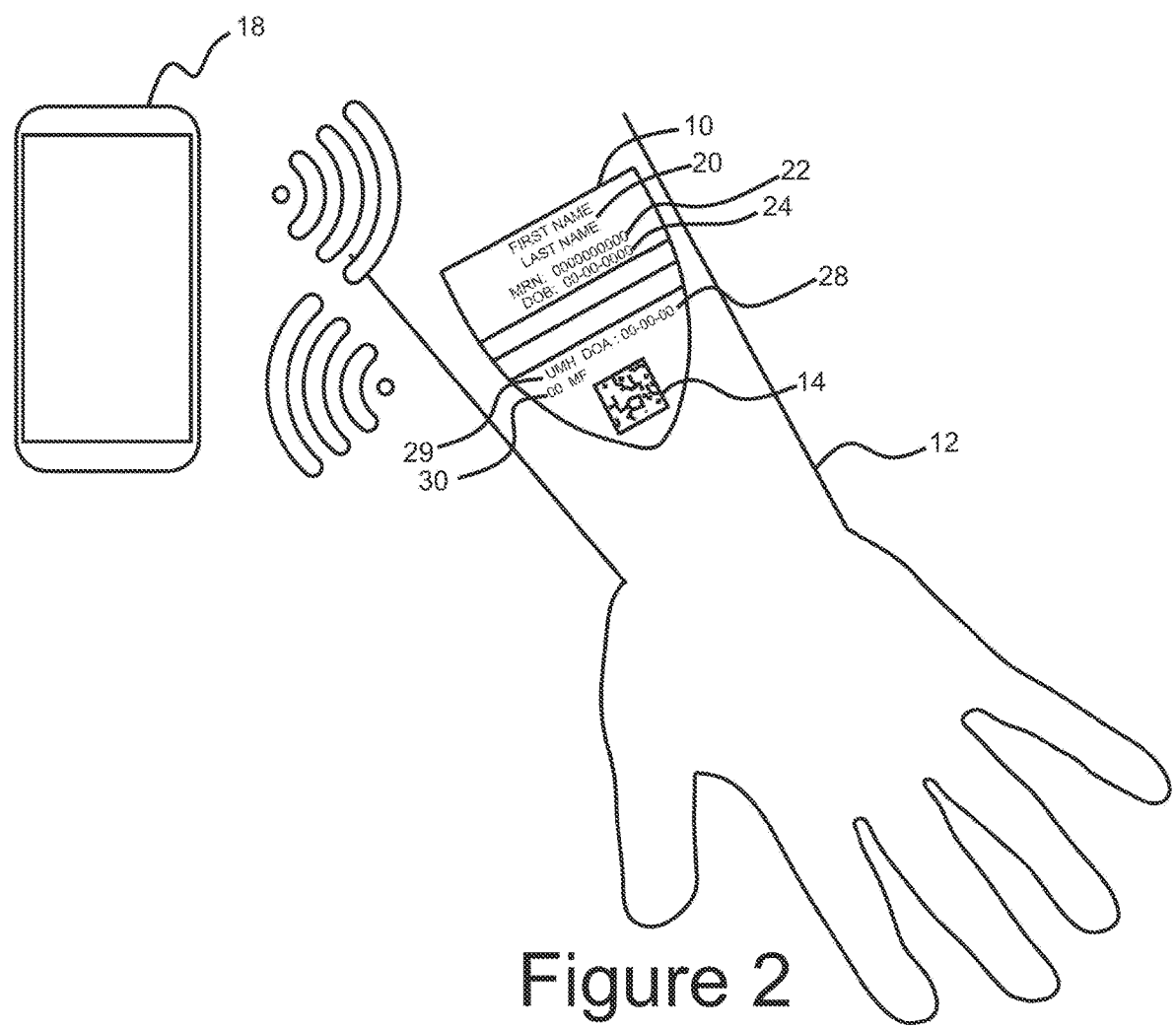
FIG. 2 shows the CID of FIG. 1 in noncontact communication with an authorized smart device.

Referring to FIG. 2, authenticated smart device 18 scans and reads code 14 on CID 10 located on the individual. This device can either be a specially built device or an internal use by a facility or a personal device used by the user. If the user uses the device the user would have authenticated the device by normal methods of logging into their phone via fingerprint or alphanumeric code. CID 10 has a unique alphanumeric identifier 14 embedded in the design.

Referring to FIG. 1, alphanumeric code 14 is transferred to the smart device 18. Code 14 offers a level of security since the number has no value or use unless there is access to data management software located on the system's secure central server. Additionally, code 14 offers a reliable way to identify the user. CID 10 may comprise additional information including first and last name 20, DOB 24 date 28 that CID 10 was printed, location of printing facility 29 and may include additional information such as preferred gender identification 30. For a user, by using an authenticated smart device as well as standard fingerprint or other unique and nontransferable authentication protocols which may be embedded in the device in conjunction with CID 10, a user can automatically authenticate and log directly into any application, native or web-based, which contains any level of secure, personal and or sensitive information thus bypassing a sometimes-onerous registration or sign-up process. Referring to FIG. 1, each user CID 10 includes the name 20 of the user, and the user's date of birth 24. A user ID number 22 also appears on CID 10. While the embodiment shown includes optically readable code 14, it is understood that any automated readable device, such as an RFID chip, a quad code, and so forth, may replace optically readable code 14. Moreover, it is noted that the system may accommodate OCR capability, which would make the generation of a machine-readable code, such as code 14, unnecessary, because the system could simply read the same information that a human operator reads but unlike a human reader, the system would process the information to provide an authorized device and user to access additional information which is not seen on CID 10.

Figure 3:
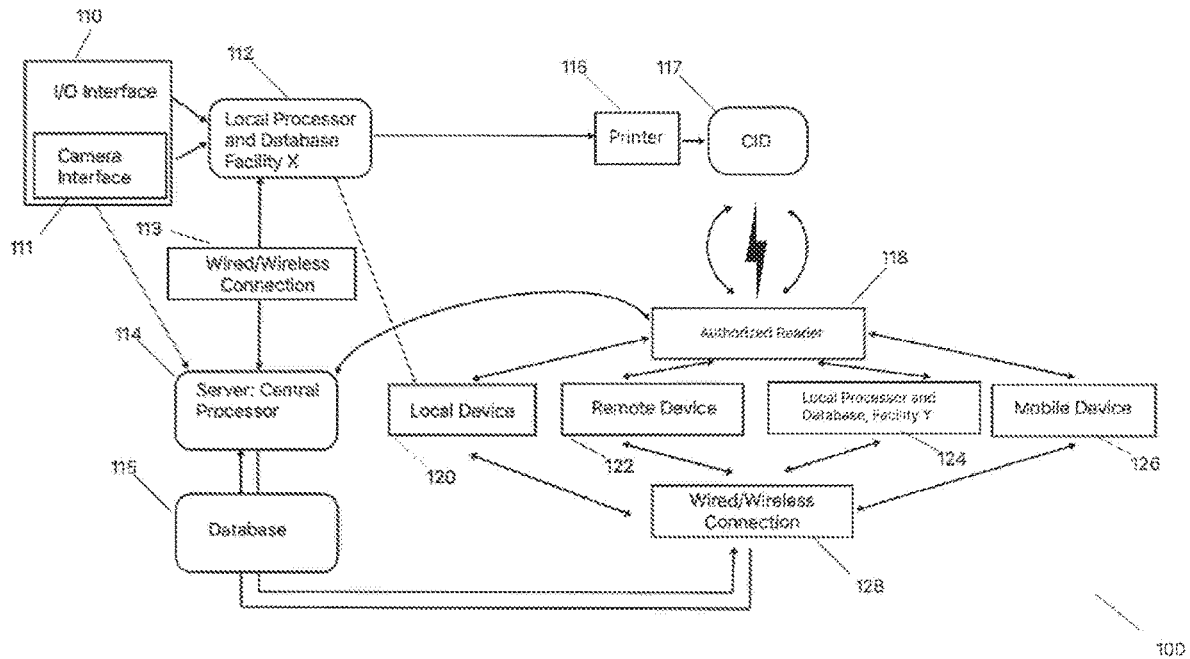
FIG. 3 shows a preferred embodiment of the system.

A hardware system constructed in accordance with the present invention and suitable for practicing the method of the present invention is illustrated in FIG. 3 with CID 10 as the nexus point of the system with servers and other devices communicating via CID 10 to administer input and share critical information. System 100 comprises input/output interface 110. I/O interface 110 could for example be a smart device, computer, etc. and would have the capability to receive human input of identifying information. Interface 110 may be linked via wired, wireless, Bluetooth, local processor/database 112, which is linked via wired or wireless connection 113 to central server 114. In an alternative embodiment, interface 110 directly connects to central server 114. Local processor/database 112 is connected to printer 116, which is capable of printing CID 10. CID 10 may interact with an authorized reader 118. Authorized reader 118 is a device that is used to interact with CID 10.

Central server 114 communicates with system 100 inputs via interface 110. Central server 114 comprises a database. Central server 114 also provides the database with user CID design information generated by a user CID design algorithm, which may be accessed, by central server 114. Such user CID design information is also stored in the database, which may be a hard drive, solid-state hard drive, or any other suitable storage medium, device, integrated sub system, and so forth.

Authorized reader 118 also allows a connected device to communicate with central server 114 for the presentation of data input screens, audio alarms, and the transmission of data to the central server 114. Reader 118 can be a non-contact communication device such as RFID or can be an optically read code (QR, bar, etc.) read by an optical code such as a camera or a red laser scanner. Reader 118 is an input and output device, which would allow a large number of mobile devices such as mobile device 126 to communicate with central server 114. In the case of smart mobile devices, such functionality is typically incorporated though there can also be a separate stand-alone reader (e.g., a mobile scanner) for devices, which do not include this function.

Reader 118 can also be connected with a local device 120 such as a medical facility glucose monitor, medical diagnostic equipment, radiology equipment and the like, or a remotely connected device 122 (e.g. home medical diagnostic equipment); facility Y server 124 (e.g. a server at a second facility), mobile device 126 (e.g. smart device that is not tethered or bound by location or individual or equipment) all of which are connected via wired or wireless connection 128 back to central server 114. Authorized reader 118 can be incorporated directly into devices 120-126 or can be an external stand-alone reader.

Input device 110, may take the form of a mini tablet, or full-size tablet incorporating a camera and connection (wired or preferably wireless) located in the admission area. Depending on the admission circumstances, when a user is being admitted, an input device 110 may be given to the user. The input device prompts the user to fill in various informational units to be used by the system. The central server 114 directly transfers this information, including an image of the face of the user, which is stored in the central server and shared via the wired or non-wired connection 113 with local server 112.

I/O interface 110 preferably includes a camera 111, which may be used to take a picture of the face of the user, for example at the time of user intake. Such picture is then advantageously displayed on the information input device during information entry to reduce the possibility of error due to misidentification of a user during data entry. Advantageously, the picture of the user and/or user name optionally remains on the screen in a fixed position as information is input into the system, for example on a personal computer or mobile device, for example a mobile device with a touch screen (such as a smartphone with an application enabling the inventive system).

In connection with the taking of the image of the user, the display on input device 110 may include a rectangle, or other shape, within which the face of the user should fit. It understood that initial input device 110 may be in a number of settings including a primary facility or any other authorized facility connected to central server 114.

Figure 4:
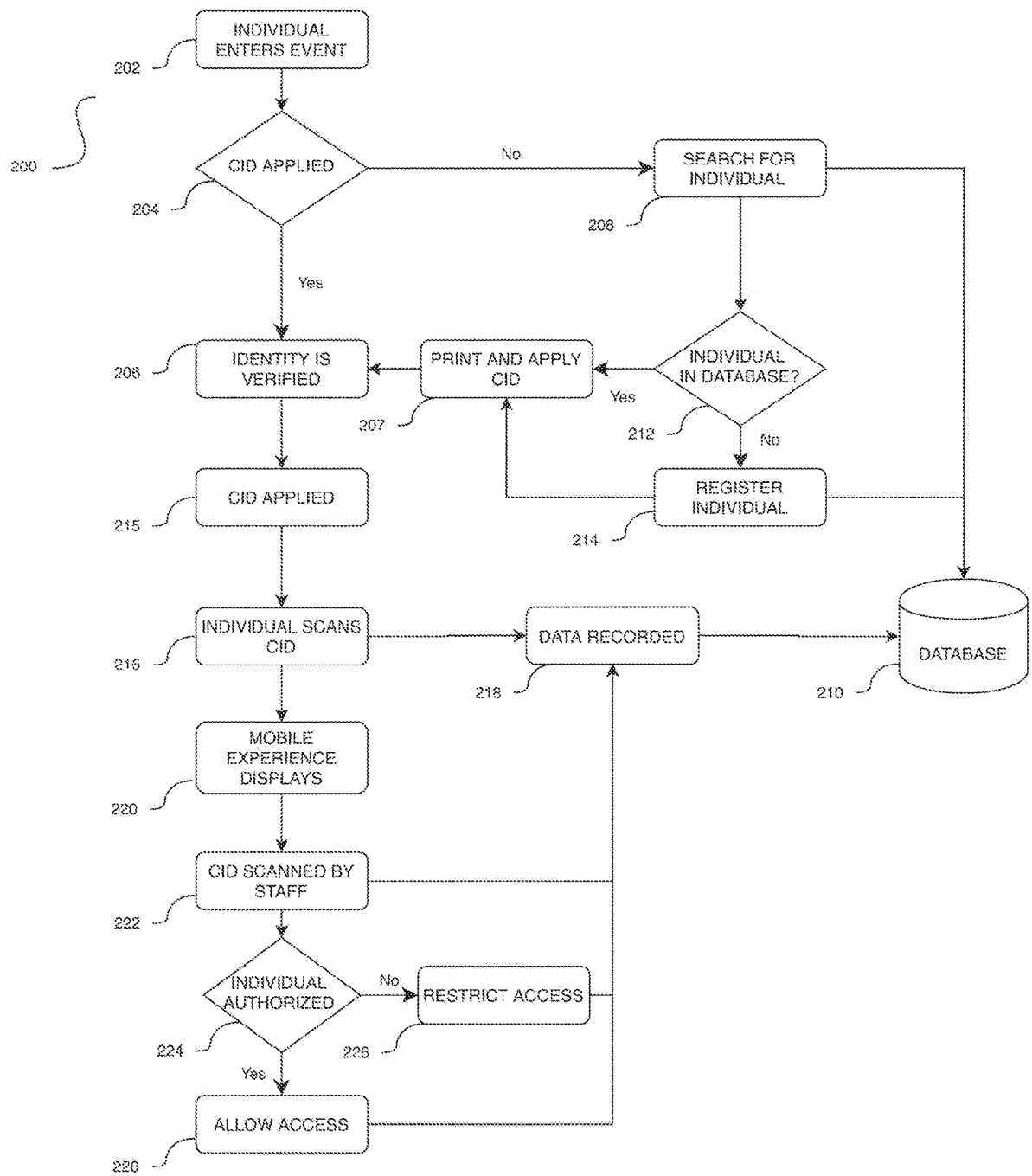
FIG. 4 is a preferred embodiment of the inventive process utilizing the system of FIG. 3 at an authorized location.

FIG. 4 is a preferred embodiment of the inventive process 200 utilizing the system of FIG. 3 at an authorized location illustrating an individual wearer's experience which begins when they physically enter 202 an authorized location for an event. An event is defined as an authorized activity at an authorized location, e.g., going to dine at a restaurant, going to shop at a store, attending a show, convention, having an appointment at a medical facility, etc.

Once the attendee arrives there is a check 204 to confirm the individual is wearing an operational and valid CID 10. If the individual is wearing CID 10, the identity of the individual is verified at step 206 by scanning CID to connect with system database 210 to confirm that CID 10 is operational and valid. Additional verification can also take place with physical verification such as government issued IDs or through digital mechanisms such as facial recognition or fingerprint.

If the badge is not confirmed to be an operational CID during the check step 204, a search is done to see if the individual is registered 208 by querying database 210 at step 212 to confirm individual's registration. If the individual is registered, CID 10 is printed and applied to the individual. If the individual is not in the database 210 as a result of the query from 212, the individual is registered at step 214 and an individual specific CID is printed and applied to the individual at step 207. The result is a verified identity specific CID 10 which is then applied to an individual at step 215. Authentication of new CIDs would preferably only be at authorized locations.

In addition to acting as a verified identification system, CID 10 can be activated to display exclusive content. In one embodiment, the registration can occur on the user's phone. By scanning the CID at an event, the CID can be paired with the event based on time and location. The attendee can register in real time using biometric verification techniques on a mobile device. When a staff member scans a CID 222, the system verifies whether the individual is authorized 224. If no, the access is denied 226. If yes, the access is allowed 228.

Once a device is registered and paired the attendee can move freely about the event. All scans of the device will be stored and documented. Staff members of the event can also scan the CID 222 to determine access to a particular sub-event, location, give-away or experience. When a staff member scans an attendee 222 authorization can be determined based on the criteria set forth in the platform. If the platform determines the attendee is not authorized access will be restricted 226. If the attendee is authorized, the system will grant access to the attendee 228.

In a preferred embodiment, in order to setup an event on the platform, a super admin must onboard the event partner. After this point, the platform is a self-service platform for the event partner to enter the information required and create an event. Once an event is created, the event partner can add sponsors and enable sponsor staff for the event. Experiences can vary based on date/time range with an option to add "counters" to clickable content (text, image/video files, hyperlinks to third-party sites and social media) that track activity by the paired CID 10 and mobile phone.

At the event, after the CID 10 is applied to the attendee, if not already activated for the event ahead of time, the CID 10 can be activated onsite through the Platform (single database and schema for multi-tenant architecture). Activation data is stored by Universal Identification (UID) in the Platform with the ability to link two (2) or more UIDs together and combine data. If the CID 10 is not provisioned for the attendee ahead of time, it can be provisioned onsite through the associated Platform or third-party database via an API. Additionally, if onsite registration is allowed by the Event Partner, the attendee or staff can register the attendee for the event.

Event staff scan attendee's CID 10 for access control and logistics and attendees can scan their CID 10 with their mobile phone to interact with the event mobile experience. All scan, form and click-through data are stored in the associated Platform and can be viewed in a real-time dashboard with export functionality. If cashless payments are enabled on the attendee's mobile phone, the attendee can scan the item for purchase and buy it on the credit card linked to cashless payments. Purchase data is stored in the associated Platform.

In a medical setting, an event is a visit to the medical facility or a telehealth visit. The user's records are stored on an electronic medical record system or user data repository, i.e. online user portal. CID 10 will be used as the primary form of identification and also as part of the three-part identification system using verbal confirmation, visual confirmation of the CID 10 with user data and electronic verification by reading CID 10 using a smart device. If all three match, then the individual is identified. Whenever there is any relevant interaction with the user during treatment/care/management whether it is prescription drugs, wound care, bath, blood work, or any other interaction that requires identification of the user, CID 10 will be scanned. Any smart device with RFID or other non-contact communication capabilities can perform this function without any additional software. This software will allow an authorized smart device with optical or noncontact communication capability to read the CID 10 whether using optical readers, RFID technology, Bluetooth or any other wireless technology available.

Figure 5:
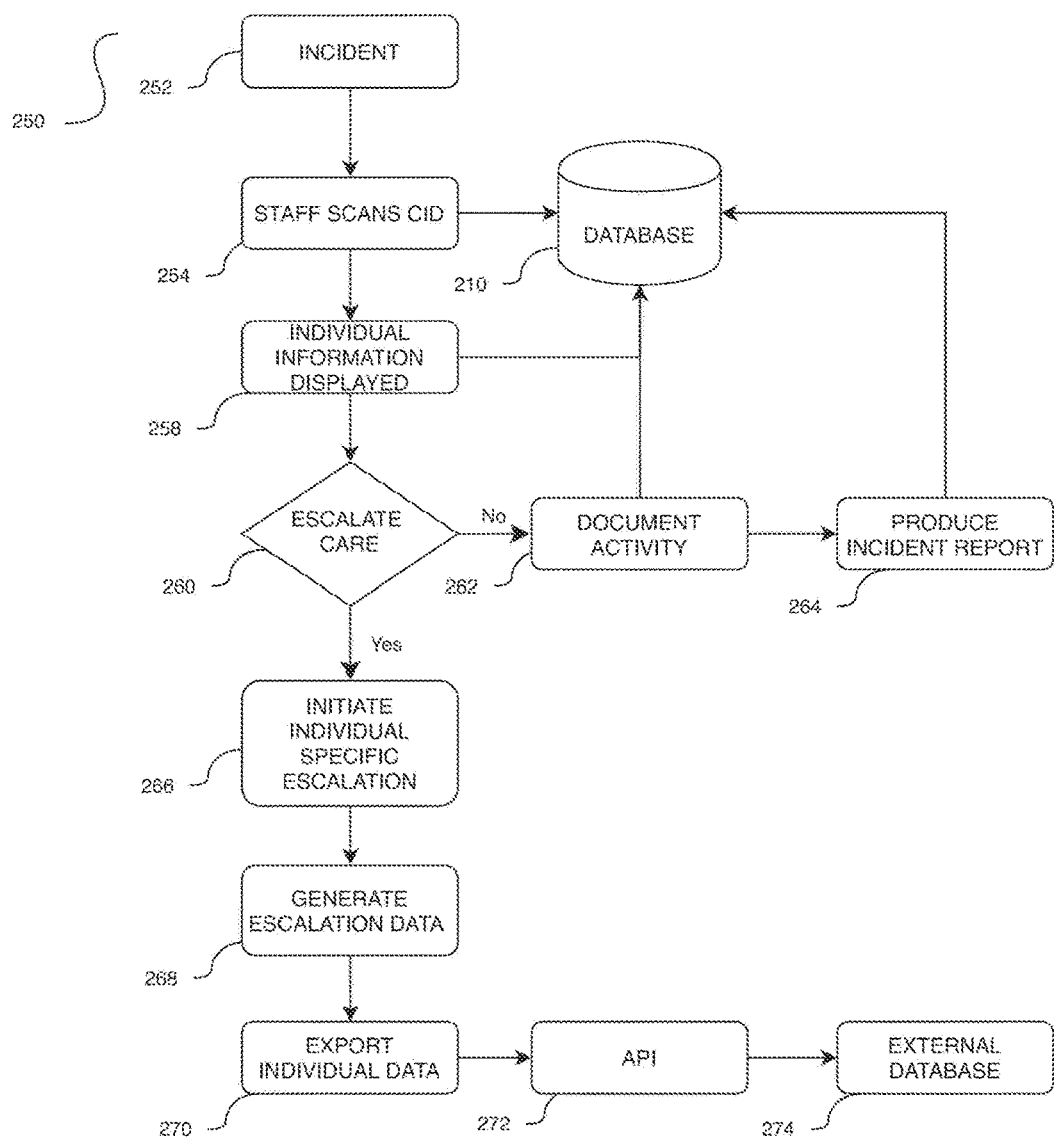
FIG. 5 is a preferred embodiment of the inventive process utilizing the system of FIG. 3 in an emergency situation outside of an authorized location.

Referring to FIG. 5, is a preferred embodiment of the inventive process 250 utilizing the system of FIG. 3 with an emergency response system which utilizes the CID 10 to identify the individual and connect to emergency response systems and provide a mechanism by which identification is verified and critical information is made available to emergency responders for the right person at the right time. Current systems cannot distinguish between the person calling emergency services and the person in need of assistance because they rely on the phone as the main identification point. The CID 10 with its inventive nontransferable identification can serve as the verification point to allow emergency response access to databases which contain detailed information that could be useful in an emergency such as allergies, emergency contact, proxy, medical insurance info, etc.

When an incident occurs 302, the staff approaches the individual and scans 304 the user specific CID 10, which has been verified and applied in FIG. 4. The scan initiates a connection to the database 210. Individual specific data from database 210 is displayed for the staff member 308. Staff can scan a CID with the mobile application to initiate an emergency response and/or report an incident. When scanned by staff 304, the associated database 310 allows access and displays digital information 308. If escalation is not necessary, the activity is documented 312 and an incident report is generated 264 which are both stored in database 210. If escalation is necessary, the staff member will initiate the escalation process 316. In a preferred embodiment, emergency services can be contacted with a single click. As part of this escalation, the system will generate escalation data profile 318. Individual data will be exported 320 to an external database 324 through an API connection 320. This function sends first responder's rich data and the platform kicks off a series of emergency workflows. This would not only be useful in general emergency situations, but also particularly useful in situations such as camping. These workflows include sending first responders a map of camper's geolocation, sending onsite personnel camper's medical information (allergies, medicines, insurance card and release form) and sending camper's parents/guardians a text with the phone number of onsite medical personnel. If emergency services button is not clicked, camp staff can view the camper's emergency contacts, medical records and release form as well as submit an incident report.

If an individual is taken to a care facility such as a hospital emergency room as a result of the incident, information from the system will be sent to these locations prior to the user arriving automating the intake process. During admission, hospital staff scan the user's CID using the CID application to view the user's health proxy information in real-time. If the user does not speak English, hospital staff can click the translate button in the CID application to use the voice and text translator to communicate with the user.

Additionally, users can scan their CID with their mobile phone to access their user portal and view certain information drawn from their admission and medical records. After discharge, users can scan their CID with their mobile phone to access their discharge information and view their ER diagnosis, expected course of illness, self-care instructions and return precautions.

Figure 6:
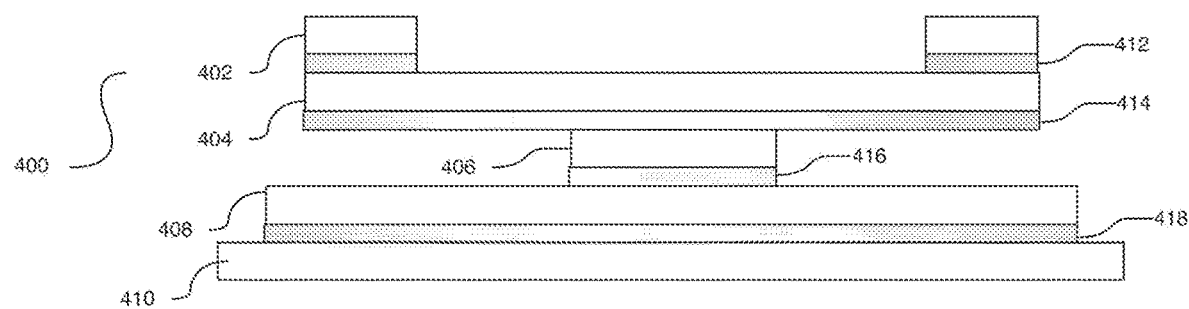
FIG. 6 is a cross sectional view a preferred embodiment of a CID.

Referring to FIG. 6 a cross sectional view a preferred embodiment of a CID 400 is shown comprising geometric frame 402, print substrate 404, electronic component 406, skin contact layer 408, carrier 410, and adhesive layers 412, 414, 416 418. CID 400 includes a thin clear flexible polymer geometric frame 402 with an adhesive 412 that attaches the geometric frame to the print layer 404. The application geometric frame 402 provides structural support to the CID prior to and during application to the skin. The adhesive coating 412 is intended to be weak enough to allow for easy removal from the rest of the device 400 after it is applied to the skin. It may encircle the outer edge of the device 400 or a portion of it. Geometric frame 402 creates the rigidity and structure necessary to maintain the structure of device 400 and its components during application to the surface of the skin after carrier sheet 410 is removed. Without frame 402 maintaining the two-dimensional architecture of CID 400 it would become deformed, wrinkled, and potentially not applicable to the surface of the skin.

The print surface layer 404 is a flexible, breathable, comfortable printable material. The printed surface layer's top surface is intended to be printed on and display the contents of the print cleanly and clearly. The printable layer 404 can include letters, numbers, designs, QR, barcode, data matrix codes and/or similar technologies for coding printable designs.

The print surface layer 404 may be opaque white, another color or opacity or watermark printed, and may have a glossy or matte print surface. The layer 404 may be printed on with laser printing, inkjet printing, thermal printing, laser etching, or other forms of printing or marking. It may be printed on multiple times. It may be prepared or treated to enhance or enable certain printing techniques. It may also be prepared or treated to prevent multiple printing. As an alternative to ink, the identification device may contain any visible marking unique to the device and the device could be paired through its marking to the identified individual.

A noncontact communication component layer 406 can connect with any smart device or reader to relay data and information from the device to another component of the system. The noncontact communication component layer 406 provides a way to transmit or receive information wirelessly. This component can be RFID, BLE or any other noncontact communication technology.

The noncontact communication layer 406 may contain an antenna or several antennas. It may contain a substrate, which may be flexible or rigid. It may contain holes, cuts, or perforations. It may also contain an integrated circuit or assembly of integrated circuits and interconnections. It may contain adhesive coating 416 on one side, both sides, or neither side. In some embodiments, the communication layer can be removed.

Geometric frame 402, print substrate 404, and electronic component 406 are placed on a skin safe adhesive layer 408 which is the layer that will come into contact with the skin when the device is applied. The thin clear flexible polymer layer 408 extends beyond the printable layer 404 to provide a smooth edge seal to the CID once applied to the skin. It also provides a flexible outer geometric frame to give the assembly flexibility when applied to the skin. The skin-safe adhesive layer 408 provides the device assembly with an interface to the skin and separation from the skin and the layers above the skin-safe adhesive layer. It provides a medium for desirable qualities in skin application such as flexibility and breathability.

All of these components 402-408 are placed on a carrier sheet 410 which serves as a stabilization layer for the printing process. The carrier sheet 410 also protects the adhesive 418 during handling before the device is applied to the skin. The backing layer is provided to hold the device prior to skin application and preserve the adhesive coating on the skin-safe adhesive layer and thin clear polyurethane geometric frame layer. It is intended to be removed immediately before the device is applied to skin. Carrier sheet 410 is treated with a release agent to allow for easy separation from the adhesive layer 408. This non-stick coating or release agent allows the rest of device 400 to be removed as a single mass. In use carrier sheet 410 is pulled off adhesive layer 408 and device 400 is applied to the patient/wearer.

Each component, the geometric frame 402, the printable layer 404, the electronic components 406 and the skin application layer 408 has adhesive layers 412, 414, 416 and 418 respectively which bond the parts to the rest of the device. The characteristics of the adhesives can vary based on the layer.

It is understood that some embodiments may not have adhesive on all interfacing surfaces. Skin contact layer 408 may contain adhesive 418 on one side or both sides. The carrier sheet 410 may comprise a coated paper or other suitable material and may be flat or have indentations or raised features in certain locations to accommodate the rest of the device assembly.

Adhesive coatings used in the device assembly may be of any suitable variety and multiple adhesives may be used in the construction of a single CID. A coating may be a combination of different coatings or a non-uniform coating. Any layer may be perforated with holes, slits or other shapes to promote the transmission of moisture and air. This moisture vapor transmission rate (MVTR) is positively impacted by perforations can affect the strength of the adhesive bond to the skin and the durability of the CID 10. The perforations may be spaced uniformly, in a pattern, or arranged according to a distribution, or arranged randomly. Perforations may also be applied selectively to areas of each layer. Perforations may be the same on each layer or different. Each layer may independently contain or not contain perforations. The perforation sizes may also be uniform, varying, patterned or sized according to a distribution, which may be random.

The thin clear flexible layer 402, print surface layer 404, noncontact communication layer 406, and skin safe adhesive layer 408 may all be realized using a material that is breathable, i.e., it is semi-permeable or permeable by vapor, gases, or moisture. The materials may be different for each layer. The noncontact communication layer may be fabricated from non-permeable materials or form a non-permeable body.

Geometric frame 402 provides structure and rigidity to the construct during application of the device and includes an adhesive layer to attach the geometric frame 402. The printable layer 404 allows for variable information to be added to the CID at may comprise visually readable and/or optically scannable data applied by dye, ink or toner. The printed information can be applied using any number of printing techniques including sublimation, thermal, laser, inkjet printing, flexographic, direct or indirect transfer. These dyes can generate visual data which can include but not limited to identifying information, name, date of birth, ticket number, identification number, employee ID, prison inmate number, scout troop number, school precinct for class trips, advertising, an image of the person wearing the inventive device and/or any other information which serves a functional, efficiency or security purpose.

The present invention contemplates printing UV long wave and short-wave dyes, fluorescent dyes, IR invisible dyes, light fast and non-lightfast dyes, glucose monitoring inks, and electrically conductive inks. Depending on the end user's need, layer 420 may comprise glow in the dark inks; inks that are activated or be visible by sunlight, UV light. The colors of the ink may change when activated by sunlight, UV light, sweat, water or other methods. Metallic ink may be used. The colors may also change over time due to exposure to oxygen. For any such inks that are not biocompatible or suitable for sensitive skins, the ink may be sandwiched between clear, biocompatible layers. Other options for ink layer 420 include thermal ink; inks that retain a charge and emit over time, with a light shined on it; inks that change their physical properties with or without particular activation; and inks that change their physical properties with or without particular activation.

To add or enhance frangibility, layer 404 can be designed in a manner wherein it is stiff and the ink is not flexible so that it pulls apart with some tension. Substrate 404 is strong and stretchable so when stretched the ink breaks apart rendering it optically unreadable and thus not transferable. Preferably, the ink also may be printed in a manner where it stretches a little to allow for movement while still allowing for optical scanning but not at all for pulling.

Printing foundation layer 404 is preferably either has properties to allow for durable printing to take place or treated with a varnish or other substance to allow for and retain any printing. The substrate 404 is durable enough to withstand application to the skin in even harsh environments yet flexible and elastic enough to be comfortable on the skin. In one embodiment, the substrate layer 404 is so thin it is almost imperceptible and only has enough durability and tensile strength to hold the components in place while on the skin.

The adhesive 414 and the substrate 404 must also have the appropriate characteristics to handle moisture either from external sources or that are naturally present on the skin, such as sweat.

Depending on the end user need, the adhesive layers can comprise a variety of materials. Suitable adhesives may include hydrocolloids, acrylic, silicone, cyanoacrylate or a combination of these adhesives. Hydrocolloids, silicones and acrylics are commonly used in skin applied applications. The adhesives can also be activated by LED, UV or electronic beam. Of particular advantage would be that UV and electronic beam activated adhesives can create a product that is not tacky when handled until activation by the user. For sensitive skin, acrylics or other pressure sensitive adhesives are preferable for skin contact. The adhesive can be added during the printing process by spraying the adhesive onto the finished product thereby applying the adhesive as part of the printing process. Cyanoacrylates are preferable for long time wear. Cyanoacrylates act on moisture and cannot be exposed to moisture or air, thus the time from application to exposure must be rapid.

In preferred embodiments, as aerosols tend to have a wide spray pattern, the cyanoacrylate would be applied at targeted zones, perhaps using pump spray or other more controllable depositing device. This could be done at the point of manufacture or by the end user at the point of use where the user would spray on or otherwise apply the adhesive then apply the device with a non-tacky surface (or tacky surface) to the recently sprayed area. The spray would be specifically designed to spray the outline of the device only. The use of spray on adhesive as the activator where the adhesive is part of the construct located on the bottom layer means that the CID is not tacky when removed from the carrier but rather is activated when comes in contact with the skin. Alternatively, the spray would activate the adhesive. Thus, the spray would be the adhesive activated by the CID when they are applied together, or vice versa the adhesive is on the CID and the spray activates the adhesive. The composition would be a liquid form of adhesive.

In some preferred embodiments, there would be a stronger adhesive on the edge meaning the adhesive on the outer layer will have stronger properties than the inner area, keeping the bond of the CID stronger at the edges, at the tension areas. This is also a way to reinforce the edges of the CID to prevent curling/peeling up.

Printable substrate 404 is suitable for receiving ink in a variety of printing processes, such as sublimation printing, laser printing, xerographic printing, inkjet printing, flexographic impact printing using a ribbon similar to an electromechanical typewriter, or conventional offset or other conventional printing processes. It is preferably of low strength and will break apart if subjected to relatively low magnitude mechanical stresses or impacts in any direction. In this application, this characteristic is referred to as frangibility. Insofar as substrate is the base for the applied inventive CID after application, its frangibility makes it substantially impossible to remove, thus adding a measure of security to the device as an identification device. More particularly, frangibility makes it substantially impossible for the device to be moved from one person or thing to another.

Printable substrate layer 404 is preferably perforated and just thick enough to bond to the adhesive and serve as the foundation for dyes and other electronic components described throughout. This will make the substrate frangible so as to prevent intact removal of the substrate or its readable components, thereby preventing transfer to another individual. The substrate must be durable enough to withstand/tolerate printing and preferably impermeable to the dyes printed thereon. Substrate 404 would also be robust enough with proper moisture vapor transmission rates, channeling and other moisture handling properties to prevent any effects from body fluids such as sweat as well as the adhesive to interfere or interact with the data layer applied to the printable layer 404 or the integrity of the entire device 400. In another embodiment substrate layer 408 will have channels on the adhesive layer to allow moisture to escape more readily.

Substrate layer 404 there may be printed visually discernable information, optically readable codes such as bar code, QR, datamatrix or any other visually machine read algorithm. The substrate layer may have a printable layer varnish which allows the printed layer to be bonded to the substrate 404. Preferably, the substrate will be no thicker than what is necessary to bond the adhesive to the lower surface of the substrate and for that substrate to carry components of layers 408 and the identifying print information on the upper surface of the substrate. The substrate is durable enough to withstand application to the skin in even harsh environments yet flexible and elastic enough to be comfortable on the skin. The substrate 404 and the adhesive must also have the appropriate characteristics to handle moisture either from external sources or internal such as sweat.

The substrate 404 itself may be white in color or a contrasting color, though other colors may prove preferable depending upon the particular application, i.e., glow in the dark, fluorescent, etc. This coloring will serve as a contrasting background making the visual data deposited on the substrate (in the next step) easier to read and more durable. As part of the printing process a white coloring may be added to the substrate 404 to create the contrasting color. Visually readable data, which can be read with the human eye, generated using skin safe dye, ink or toner can be applied using any number of printing techniques including sublimation, thermal, laser or inkjet printing. These dyes can generate visual data which can include but not limited to identifying information, name, date of birth, ticket number, identification number, employee ID, prison inmate number, scout troop number, school precinct for class trips, and any other environment where identifying information serves a functional, efficiency or security purpose. For security and authentication these dyes can also could include but not limited to UV longwave and shortwave dyes, fluorescent dyes, IR invisible dyes, light fast and non-lightfast dyes, nano-sized RFID, Bluetooth®, BLE or other noncontact communication chips, glucose monitoring inks, electrically conductive inks which when attached to a microprocessor or microchip and a power-source can complete an electrical circuit. The printable substrate 404 may also comprise dye or inks that change their physical properties. activated by perhaps by ambient light, activating light or sunlight.

Data codes can be added as part of the visual display printed layer 404 such as Quick Response (QR), data matrix, bar codes or any other algorithmic code can be read with an optical electronic device can also be added to the construct. These codes will allow an optical electronic reader to pull unique identifiers from the device. These identifiers can be randomly generated codes which when used with a data management system will allow identification, tracking or data manipulation. These codes can serve as a secure form of data communication allowing the reader to pull information from the skin worn device and also communicate back with the device. Given the prevalence of optical visual code readers, the interaction between these codes and the individual can serve any number of purposes for the wearer of the skin device and/or a third party reading the device.

To maximize reliability of printed optical information components, substrate 404 may be white or have a color that contrasts with the printed information. Glow in the dark, fluorescent, etc. coloring may be advantageous depending upon conditions of use. As an alternative to having a white or colored material serving as a substrate, the printing process for applying printed information may further comprise applying a white background pigment to the substrate to create contrast.

Adhesive layer on the non-printed side of substrate 404 attaches to electronic device 406 (e. g., RFID OR Bluetooth inlay) which bonded/married to the electronic device substrate layer. The electronic device 406 may include electronic components i.e., electronically readable, devices such as electrical circuits, processors, resonant, RFID OR Bluetooth devices, UHF (for long distance reading) or NFC, noncontact communication devices, antennas, microchips, printed circuitry, flexible paper batteries, printed battery, sensors or other printed or nano-printed electronics. In some embodiments, the device or sensors are powered by a battery that is charged by the user's body heat or electricity created by the user's body.

In accordance with a preferred embodiment of the invention, a passive RFID OR Bluetooth device 406 comprising a chip and printed circuit antenna are provided. Preferably, the substrate is no thicker than what is necessary to support adhesive and informational components under normal wear and tear, but thin enough to be frangible upon the application of force during, for example, an attempt to remove the device.

Wireless device 406 may be any electronically readable device such as an electrical circuit, processor, resonant circuit, active or passive RFID OR Bluetooth device (optionally a nano-sized RFID OR Bluetooth chips), UHF, NFC, wireless communication devices, antennas, microchips, printed circuitry, printed battery, sensors or other printed or nano-printed electronics. The electronic device can also be shaped in a way that has aesthetic value such as a butterfly, diamond, sun or flower. For example, the device inlay antenna can be in the shape of a diamond. This diamond shape has aesthetic value when seen through the printed and substrate layer, functional effectiveness, and serves as a visual cue for status or access to a particular location. For example, a circular shape allows access to the facility, a diamond shape allows access to the VIP section. Other shapes can be used depending on the desired uses. Additional aesthetic additions can include textured material. Perforations can also be added to add aesthetic and functional value as described above.

Electronic devices 406 may use noncontact communication technology such as RFID OR Bluetooth, UHF or NFC and other non-contact communication devices. The electronic device 28 may include electronic components i.e., electronically readable, devices such as electrical circuits, processors, resonant, RFID OR Bluetooth devices, noncontact communication devices, antennas, microchips, printed circuitry, printed battery, sensors or other printed or nanoprinted electronics. A wireless device may be any electronically readable device such as an electrical circuit, processor, resonant circuit, active or passive device (optionally nanosized chips), wireless communication devices, antennas, microchips, printed circuitry, printed battery, sensors or other printed or nano-printed electronics.

Types of RFID OR Bluetooth and Bluetooth protocol enabled devices include Low frequency RFID OR Bluetooth, Near Field Communication RFID OR Bluetooth, Ultra High Frequency RFID OR Bluetooth, and Bluetooth Low Energy (BLE). These microchips can store significant amounts of information. These identifiers can be randomly generated codes which when used with a data management system will allow identification, tracking or data manipulation. These codes can serve as a secure form of data communication allowing the reader to pull information from the skin worn device and also communicate back with the device. Given the prevalence of near field communication or ultra-high frequency RFID OR Bluetooth and Bluetooth readers, such as smart phones, tablets, watches and the like, the interaction between these technologies and the individual can serve any number of purposes for the wearer of the skin device and/or a third party reading the device. In certain embodiments, an MRI compatible power source for non-contact communication (such as RFID OR Bluetooth or Bluetooth compatible components) would be embedded in the CID. MRI compatible metal or palate batteries would be used in connection with the CID to enhance functionality. The non-contact communication device could provide constant connection to other Bluetooth compatible components.

These devices can also contain a variable rolling code which would increase the security and functionality of the device by creating a counter within the chip that will prevent anyone from accessing or using the chip without the proper rolling code at that particular moment.

Electronic components 406 add a level of security and functionality over optically read codes. These devices can store more information, be reprogrammed, keeping a rolling count of the number of times the device was read and a variable rolling code for authenticity to increase the security of the CID. This functionality creates any number of advantages given the application. The rolling code in addition to counting can also dynamically tailor the information being displayed based on the count or number of times the CID is read. For example, on the first read an instructional screen can be provided to educate the user. On the second read the instructional video can be replaced with a highlighted tutorial and on the third read the instructions are replaced with a link to more information. Furthermore, nano-sized electronic particles can be added at this stage used to confirm the authenticity of the skin worn device. In another embodiment, a flexible metal sheet would serve as the substrate layer and an electronic could be printed thereon. print on the metal itself. In preferable embodiments, the electronic would have to have a white layer on it. Data processors such as circuits, microchips and microprocessors can be added to the device in conjunction with a conductive ink to create a skin wearable computer-processing unit.

These components can be used to determine whether CID 400 has been tampered with or removed from an individual. This concept is known as physical frangibility. In addition, to the physical frangibility, whereby when the product is removed it is inoperable, the functionality of the device can be limited or ceased based on the variables unrelated to the physical state creating a nonphysical frangibility. The device using a combination of electronic components and software can determine when a CID has been removed from one person and applied to another. Security components such as holograms can be added in the final step for authentication. Sensors may also be used. For example, a weight scale in a bathroom would not transmit data to a home health wireless receiver unless the CID identity and RSSI value was greater than −70 (for example). Thus, the data in guests in the house using the weight scale would not be transmitted to the home health hub.

Figure 7:
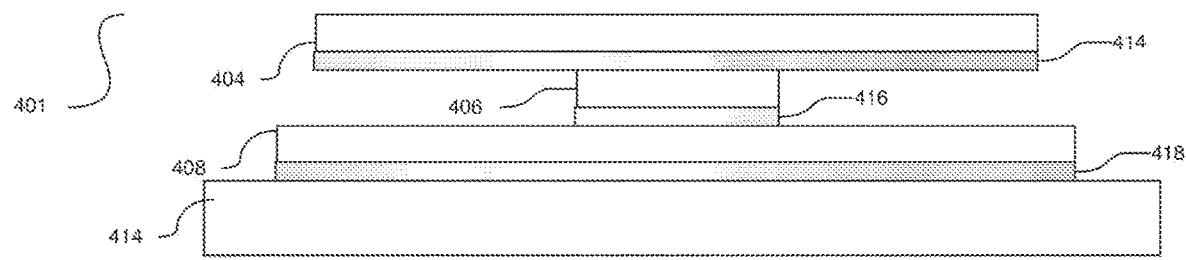
FIG. 7 is a cross sectional view a preferred embodiment of the CID shown in FIG. 6 once it has been applied to the skin.

FIG. 7 shows the CID as shown in FIG. 6 once it has been applied to the skin 414. It no longer contains a paper application geometric frame 402 or carrier sheet 410. The remaining layers on the skin are the print surface layer 404, noncontact communication layer 406, and skin safe adhesive layer 408. The layers may bend and conform to the skin once applied to the skin 414 using pressure.

Once device 401 is applied to the skin, Geometric frame 402 can be removed and discarded. The frame 402 can encompass all or part of the surface area of the construct. Frame 402 also can create a window by which the point of service printing of variable data can take place. This window is needed to allow the printer to apply the necessary data directly onto print ready substrate 404 for visual and optical reading. For use in healthcare, activation of the QR code on device 400 would link to the Patient Portal.

In an alternative embodiment, the noncontact communication component layer is placed between the print surface layer and the breathable substrate layer. The breathable substrate with skin safe adhesive layer also functions as both the breathable substrate layer and skin-safe adhesive layer in FIG. 6. The breathable substrate with skin-safe adhesive layer may be a single layer or combination of several layers. Once applied to the skin, it no longer contains the paper application geometric frame or carrier sheet. The layers may bend and conform to the skin once applied with pressure to the skin.

In an alternative embodiment, no breathable substrate layer or skin-safe adhesive layers are present. The adhesive coatings on the print surface layer and noncontact communication component layer are chosen to be skin safe adhesives.

In an alternative embodiment, the CID may have two layers of adhesives one that captures the sensor on the body, and the second layer of adhesive that at the point of care is printed on with the patient information and is applied over the first layer as part of the admission process for visual identification In an alternative embodiment, the breathable substrate layer is made smaller compared to the print surface layer.

This is done to alter how the layers bend when conforming to the skin, creating a different tapered effect compared to the device assembly in FIGS. 6 and 7.

In an alternative embodiment, a single layer provides the functionality of the printed layer and breathable substrate layer.

The printable material layer 404 is designed to accept printing such as inkjet or laser printing. It may lay flush with the printer feed page's top surface to ensure even printing. The skin contact layer 408 and noncontact communication assembly layer 406 are included in the embodiment shown in FIG. 7 as examples of component layers that may be included in a CID. Any assembly may be the CID present on the printer feed page instead, or any other combination of layers and materials, and components that constitute a skin-applied applied device assembly.

The printer feed page may be made from printable paper or a material not intended for printing. It may also be printed on during the printing process or may be excluded from printing. It may come as a sheet or as part of a roll. The printer feed page may be coated to function as a removable backing or may supplement a removable backing included in the CID. There may be adhesive coatings on or between any surface of the layers in the CID. The print media format may contain multiple CID assemblies of similar or varying composition.

CID 400 may be affixed to the skin with acrylic adhesive or a gentler softer silicone adhesive. In an alternative embodiment, the geometric frame does not include a substrate and a skin safe layer located closest to the skin is the only layer that comes in contact with individual when CID is applied to the skin.

Figure 8:
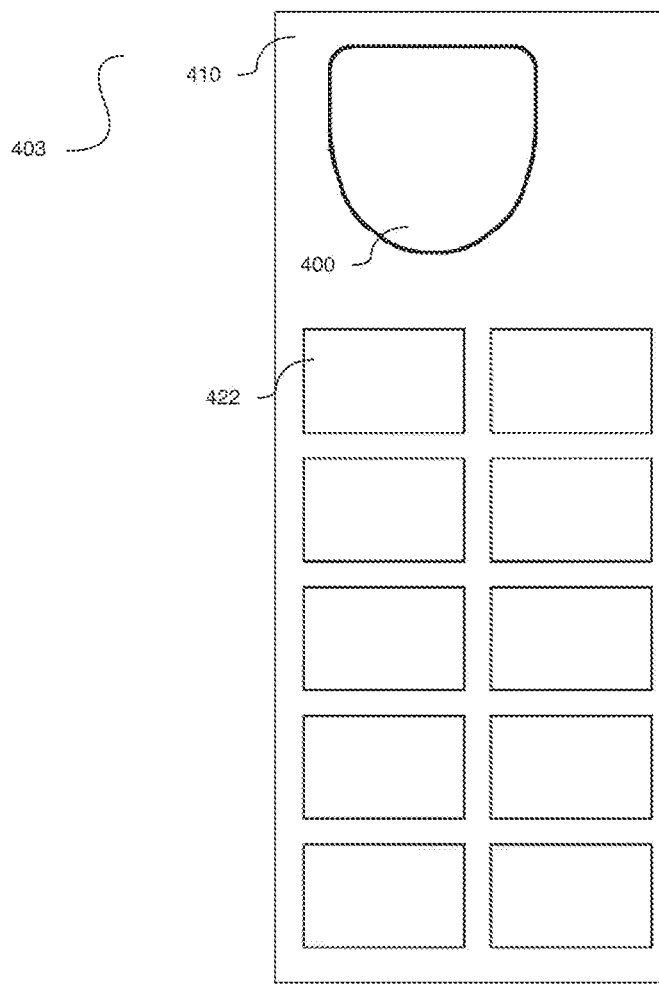
FIG. 8 is a top view of the carrier sheet in FIGS. 6 and 7, including the single CID and additional labels.

FIG. 8 is the top view of a CID 400, carrier sheet 410 and printed labels 422 in a single layout 403. In this embodiment the carrier sheet 414 also has space for additional identification labels which can be used for skin application or not. These labels 422 can be printed at the same time as CID. They can include specific information about the wearer of the CID or the facility producing the CID.

The contents printed on the skin-applicable identification may be automatically coordinated with the contents on the identification labels. One or multiple skin-applicable identifications and identification labels can be printed on a page. Either may be omitted from the backing print media. The location of the skin-applicable identification and identification labels may be changed to accommodate different sizes or numbers of either. The materials including adhesives used for skin-applicable identification and identification may differ or be the same.

Figure 9:
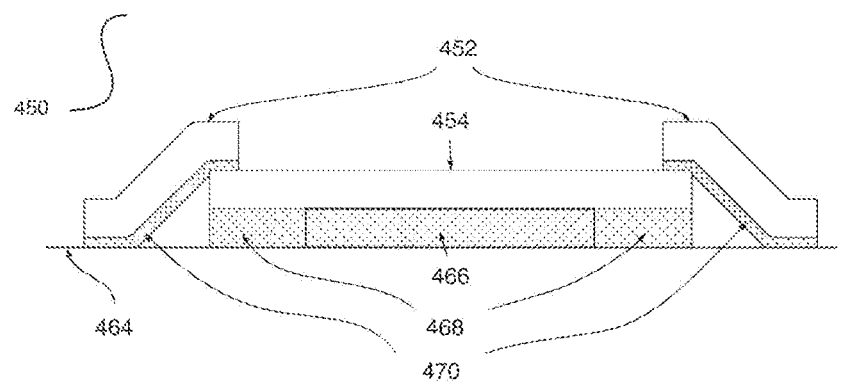
FIG. 9 is a cross-sectional view of an alternative embodiment of a CID comprising multiple adhesives used within a single CID assembly.

FIG. 9 shows a cross-sectional view of an alternative embodiment of multiple adhesives used within a single CID 450 assembly. It contains three adhesives: a first adhesive 466, a second adhesive 468, a third adhesive 470. It also includes a printable material layer 454 and a geometric frame 452. The three adhesives applied selectively can be configured to optimize performance for feel, flexibility, durability or other set of requirements. An example configuration is a weak adhesive with high tack as first adhesive 466, a stronger adhesive as second adhesive 468, and thinner layer of third stronger adhesive 470. This configuration would allow the CID to form a tight seal to the skin around its perimeter but allow for gentler feel and conformability in the center region of the CID. The geometric frame 452 provides a material taper that prevents the edges of the skin-contact device assembly from peeling off the skin due to friction or other forces. It provides a means to create closer conformity to the shape of the skin than an equivalent device where third adhesive 470 and the geometric frame 452 are not present, even if second adhesive 468 is made thinner to create a tapered effect. The geometric frame 452 may be made from other material to achieve a tighter seal or stronger edge protection.

The three adhesives 466, 468 and 470 may be each distinct, or two of the three adhesives may be the same. The thickness may be different for each adhesive. More adhesives types may be added. The adhesives may be non-uniformly or uniformly applied within their regions. It is understood that an alternative design of a CID may have more or different layers than those presented above.

Figure 10:
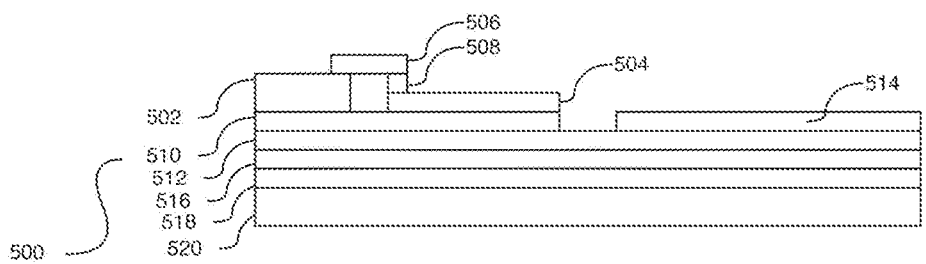
FIG. 10 is a cross sectional view a preferred embodiment of a CID.
Figure 11:
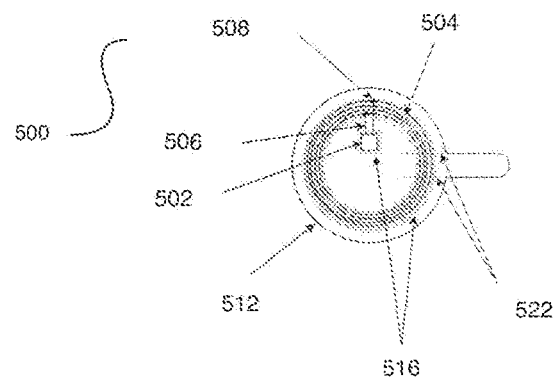
FIG. 11 is a top view a preferred embodiment of the CID shown in FIG. 10.

Referring to FIGS. 10 and 11, CID 500 comprising Bluetooth IC 502, fragile foil/wire noncontact communication antenna 504, connection pin 506, conductive adhesive 508, an adhesive layer 510, elastic material 512, nondeformable or rigid ink 514, adhesive layer 516, release layer 518, paper backer 520, perforations 522 where Bluetooth IC 502 is connected to fragile foil/wire noncontact communication devices such as RFID or Bluetooth antenna 504 using its connection pin 506 and rigid connection such as a conductive adhesive 508. The built-in frangibility of the electronic component ensures that the removal will render the electronic device inoperable and ensure that the electronic component cannot be reused. In other embodiments, it may be beneficial to keep the electronic components intact upon removal so that the area can be observed and cleaned and then the sensors can be used again with reauthentication. For example, the removal can trigger a sensor alarm when there are not readings on the sensor from the skin and the sensor. Reauthentication can be done in a number of ways including sensor readings verifying biorhythm remains virtually unchanged. Thus, instead of mechanical frangibility, functionality of the CID can be determined by comparing data from sensor readings.

An adhesive layer connects the Noncontact communication device 502 such as RFID or Bluetooth IC and fragile foil/wire noncontact communication device such as RFID or Bluetooth antenna 504 to the first surface of a non-resilient deformable flexible and elastic material 512 such as silicone or hydrocolloid layer, which may also a polymer layer. A non-resilient deformable/rigid printed layer may also be applied to the non-resilient deformable flexible and elastic material 512 such as silicone, hydrocolloid or another polymer layer. The flexible and elastic material 512 such as silicone, hydrocolloid or another polymer layer has an adhesive layer 516 applied to its second surface. A release layer 518 resides between a paper backer and the adhesive layer 516 applied to the non-resilient deformable polymer (e.g., silicon) layer 512. The paper backer 520 serves as a delivery medium before application. The dotted lines 522 represent perforations that will tear upon removal of the device from the skin. The dotted lines 522 can also represent full die cuts through the substrate layer 512. When device 500 is removed from the skin the perforations 522 ultimately leads to tearing of the substrate material 512 and the antenna 504 rendering the electronic component inoperable.

The placement and layering specifics of the RFID or Bluetooth sub-assembly 502-506 and the wearable substrate sub-assembly may be altered to accommodate additional layers or modifications to either the Noncontact communication device such as RFID or Bluetooth sub-assembly or wearable layer sub-assembly. This includes the addition of additional processing, energy sources, information displays or additional transmitter/receiver assemblies.

The Noncontact communication device 502 such as RFID or Bluetooth IC can have a different pin location or be oriented differently. The frangibility mechanism would not be reliant on a specific Noncontact communication device such as RFID or Bluetooth IC packaging or orientation. The cut 522 may be a weak point, perforation, or cut such that when sufficient force is applied, possibly during removal from the skin, to the weak points of the noncontact communication device the device is disable. When the device is peeled, pulled or attempted to be removed from the skin, that force necessary to remove the device disables the device or records the tampering of the product. The device is disabled by physically breaking weak points in the closed-circuit necessary for the device to function when removal is attempted.

There may be additions to the non-resilient or deformable polymer layer in order to increase the effectiveness of frangibility. The perforation or cuts give additional guidance to the point of bending around rigid connections. There may be a gap in adhesive application to aid separation or stress on the connection point.

The flexible and elastic material 512 such as silicone, hydrocolloid or another polymer layer has an adhesive layer 516 applied to its second surface. A release layer 518 resides between a paper backer 520 and the adhesive layer 516 applied to the non-resilient deformable silicon 512 or another polymer layer. The paper backer 520 serves as a delivery medium before application.

An extension of substrate material 512 can work in conjunction with cuts or perforations in order to enhance frangibility or add additional points by which a rigid or fragile construction may be targeted. There may be different designs for perforations, not just straight lines but any design suited to the job.

In accordance with the present invention, it is contemplated that the RFID or other noncontact communication device may use any one of a number of strategies to communicate. For example, the device may be passive. Alternatively, the device may include a battery or a capacitor as a power source. Likewise, the device may utilize the harvesting of electrical power from ambient electrical fields or be powered by electricity generated across a thermal gradient. These various power structures In preferred embodiments, there will be at least two sensors, where one is used for measuring a vital sign (e.g., temperature) to monitor the patient and a second sensor would measure another vital sign to sense tampering, removal or malfunction of the device so that a signal could be sent to the central server to send an alarm to the system and to users or providers. The device could also be deactivated if a sensor detects attempted removal, tampering and sends a signal The visible marking would be uniquely tied to the person. In a preferred embodiment, the device would comprise an RFID component (or other NFC device) having a signaling range 2-8 inches, preferably and a Bluetooth having a signaling range of 5-10 meters. In preferred embodiments, the device would be activated using RFID. Using Bluetooth, the CID pairs to the phone or other smart device and transfers the MAC address of the electronics in the CID. In preferred embodiments, the device would have physical dimension ranges 22 mm-50 mm diameter×3.2 mm-6 mm high and a weight range of 3-15 grams. For uses where continuous monitoring is required, once paired, if the system detects tampering or malfunctioning of any sensors or other parts, the system may automatically deactivate the device and send an alarm. The system may also deactivate the device for any unauthorized use. By using Bluetooth, the identity of the patient can be verified and sensor data can be captured by an authorized device. This can be used as a substitute for the visible marking. The caregiver would not have to be in close contact with the patient they could be 30-40 ft away. This is particularly useful with physiological sensors that are placed on the body to capture physiological data and are typically under the clothing. Additionally, it would be very useful in quarantine situations where vital signs can be taken from a safe distance.

Additionally, the device can send out a signal to allow passive reading from distance. In this scenario an individual can enter a room and the device will immediately notify the appropriate devices of the person's presence. Other possibilities include thermoelastic (that is the generation of electricity by converting thermal energy into mechanical tension, which is then converted into electrical energy, for example by a piezoelectric crystal. Likewise, vibration from a person walking, or the like may drive piezoelectric power generation.

For powering on the chip, various techniques utilized in low-power electronics may be employed. One mechanism which may be advantageously employed is a sleep timer that schedules a power on at intervals to do an operation or several operations, but then totally shuts down and spends most of its time idle, consuming little power. Alternatively, the storage media's level of charge can trigger a chip-on event. Another alternative is to use any source of incoming harvested energy to trigger the chip to go on. For example, this can be an outside event like RFID reading, you can incorporate a sensor that will trigger the chip to turn on.

Figure 12:
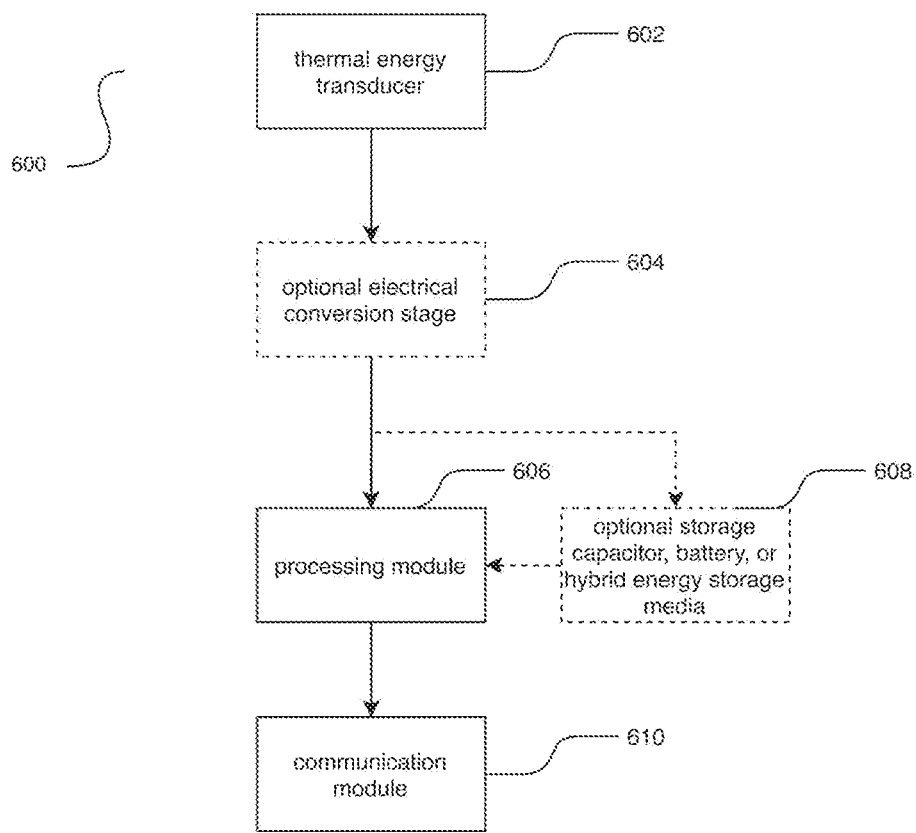
FIG. 12 is a schematic for thermal energy generation to be used in connection with a CID.

FIG. 12 shows a block diagram 600 for thermal energy generation as may be used on a CID with the following elements thermal energy generator 602, an electrical conversion stage 604, a processing module 606, an energy storage module 608, and a communication module 610. Thermal energy generator 602 may be a thermoelectric generator such as a Seebeck generator or Peltier cell converts energy based on a thermal gradient. The thermal gradient may be present due to difference in temperature between the surface of human skin and the ambient temperature. The thermal energy generator may also be a thermoelastic generator or a transducer for converting strain, force, or pressure into electrical energy and may be realized with a shape memory alloy such as nitinol, constricted with surrounding structure or material and generate tension. The tension may be converted to electrical energy by a physically coupled mechanical electrical transducer, such as a piezoelectric transducer which may be flexible or rigid and made from organic, inorganic or a combination of materials. The electrical energy generated may be converted in an optional voltage or other electrical conversion stage 604. The stage may limit, condition or convert characteristics of the electrical energy, such as frequency, voltage, current, input impedance, or output impedance. The conversion stage may be formed from multiple combinations of cascaded or parallel connected conversion stages or bypassed altogether. The electrical energy will then power a processing module 606, such as a micro controller, application-specific integrated circuit (ASIC) or combination of processing modules. Electrical energy may also be supplied to an optional energy storage module 608 such as a capacitor, super capacitor, battery, or combination. The storage media may be controlled by the processing module 606, a separate processing unit, or be self-controlling. The storage system may also be omitted. The processor module sends data, control signals, or a combination to a communication module 610 such as a wireless transmitter, receiver, transceiver, display, light source, audio source, touch screen, actuator, sensor or combination thereof. The processing module may also control the level of energy delivered to the communication module. The communication module 610 may also send data or control signals to the processing module 606.

Figure 13:
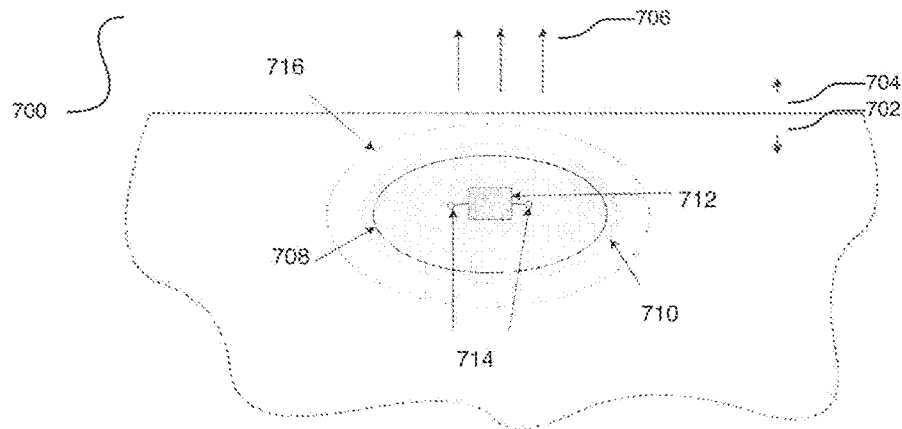
FIG. 13 shows a top partial perspective view of an alternative embodiment of a CID comprising an assembly for harvesting energy.

FIG. 13 shows an assembly 700 for harvesting energy from a temperature gradient at the interface of a human body 702 and ambient air temperature 704 creates a heat transfer convention 706. A shape memory alloy 708 is present and its shape is physically constricted. The tension produced by the shape memory alloy 708 is converted into electrical energy using an electromechanical transducer 710, which may be piezoelectric or nitinol. The energy is transferred to an electronic device, electronic storage medium 712 such as a battery, or combination thereof with a device power connection 714. A skin contact assembly 716 consisting of an adhesive, polymer or combination thereof provides a means to couple the device 712, shape memory alloy 708, and electromechanical transducer to skin 710.

Figure 14:
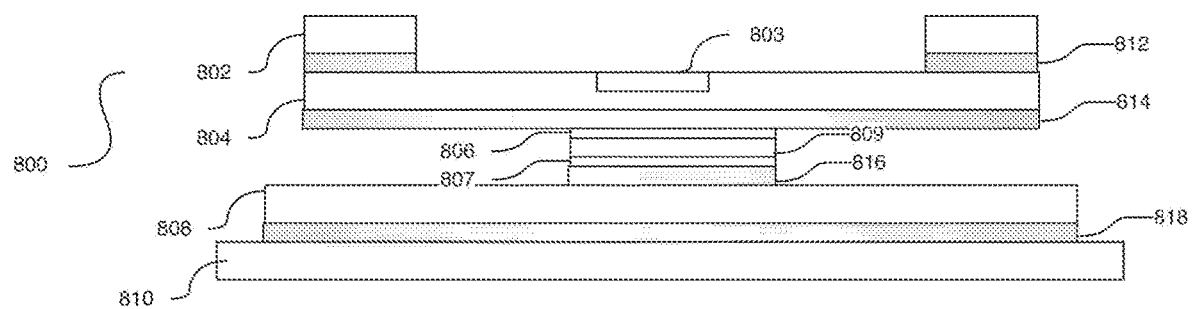
FIG. 14 is a cross sectional view a preferred embodiment of a CID used to monitor vital signs in the field.
Figure 15:
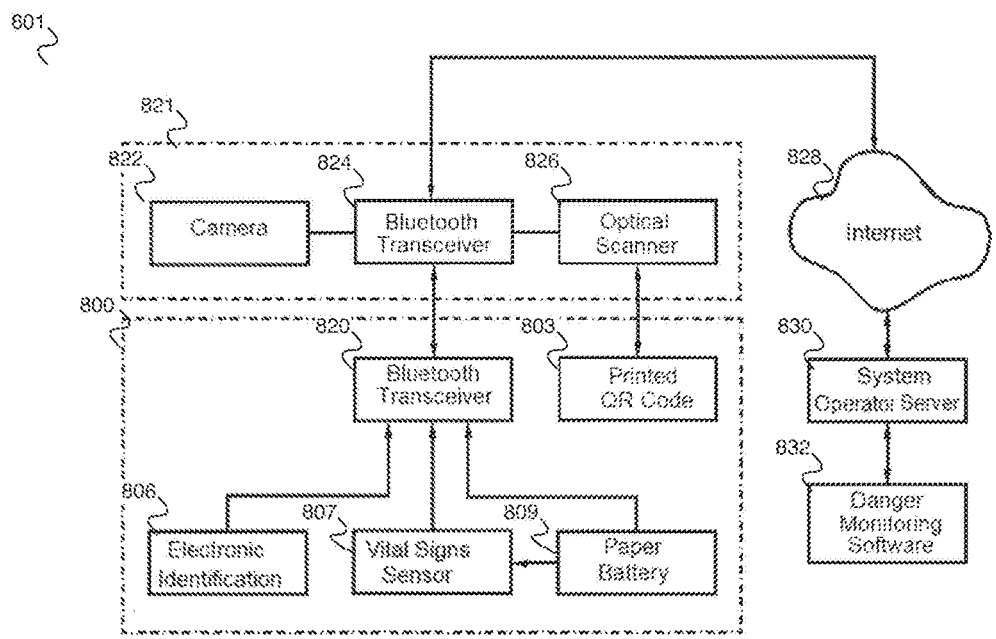
FIG. 15 is a schematic of the system used in connection with the CID shown in FIG. 14.

Referring to FIGS. 14 and 15, an alternative embodiment of a CID and associated system is shown which can be used in the field to monitor the health status of a person while in custody. Referring to FIG. 14 a cross sectional view a preferred embodiment of CID 800 is shown comprising geometric frame 802, print substrate 804 comprising optically scannable code 803 such as a QR code, electronic component 806 comprising least one sensor 807 that continuously monitors vital signs such as pulse oxygenation and heart rate and a battery 809, skin contact layer 808, carrier 810, and adhesive layers 812, 814, 816, 818. CID 800 includes a thin clear flexible polymer geometric frame 802 with an adhesive 812 that attaches the geometric frame to the print layer 804. The application geometric frame 802 provides structural support to CID 800 prior to and during application to the skin. The adhesive coating 812 is intended to be weak enough to allow for easy removal from the rest of the device 800 after it is applied to the skin. It may encircle the outer edge of the device 800 or a portion of it. Geometric frame 802 which creates the rigidity and structure necessary to maintain the structure of device 800 and its components during application to the surface of the skin after carrier sheet 810 is removed. Without frame 802 maintaining the two-dimensional architecture of CID 800 it would become deformed, wrinkled, and potentially not applicable to the surface of the skin.

The print surface layer 804 is a flexible, breathable, comfortable printable material. The printed surface layer's top surface is intended to be printed on and display the contents of the print cleanly and clearly. The printable layer 804 can include an optically scannable code 803 which may be letters, numbers, designs, QR, barcode, data matrix codes and/or similar technologies for coding printable designs. The print surface layer 804 may be opaque white, another color or opacity or watermark printed, and may have a glossy or matte print surface. In a preferred embodiment, it is prepared or treated to prevent multiple printing.

A noncontact communication component layer 806 can connect with any smart device or reader to relay data and information from the device to another component of the system. The noncontact communication component layer 806 provides a way to transmit or receive information wirelessly. This component can be RFID, BLE or any other noncontact communication technology. The electrical identification layer 806 may contain an antenna or several antennas. It may contain a substrate, which may be flexible or rigid. It may contain holes, cuts, or perforations. It may also contain an integrated circuit or assembly of integrated circuits and interconnections. It may contain adhesive coating 816 on one side, both sides, or neither side. In some embodiments, the communication layer can be removed. The vital signs sensor 807 takes biometric measurements from the surface of the skin. A paper battery 809 powers the electronic components 806 and/or 807. In an alternative embodiment multiple different adhesives could be used to secure the different components. The sensors and battery and components would be secured to the device with a strong adhesive while the edges of the device would be used to secure the CID to the skin. This would increase the comfort while keeping the sensors in place to take accurate and consistent data.

In an alternative embodiment, device 800 could be removed from the skin to replace adhesive layer 812 for longer use of the device. This would give an opportunity for direct visual examination of the area by the wearer or others, such as a medical professional. Security would be maintained with a two factor authentication by pairing with the user's previously authenticated device (e.g., phone, tablet, smart device) and by monitoring biometric data (e.g., signature of circadian rhythm) to create a unique biometric signature to authenticate the single user, where any removal and attempted repairing of the device would fail. In a preferred embodiment, biometric factors can be used to confirm identity. To maintain security, there would be a pre-set time limit on the non-contact of the sensors to the skin. In preferred embodiments, the defined period of time would be set under 30 mins, preferably under 10-20 mins. Beyond that there would be an alarm sent to the system noting that the device would be deactivated without biometric reauthentication. In a preferred embodiment, biometric sampling (e.g., a combination of heart rate, temperature, pulse oximetry) would occur every 3-5 mins or so. Reauthentication is complete when the new data is compared to previously recently sampled data. In preferred embodiments, the body temperature measurement is accurate within +/−0.1 degree.

Geometric frame 802, print substrate 804, and electronic component 806 are placed on a skin safe adhesive layer 808 which is the layer that will come into contact with the skin when the device is applied. The thin clear flexible polymer layer 808 extends beyond the printable layer 804 to provide a smooth edge seal to CID 800 once applied to the skin. It also provides a flexible outer geometric frame to give the assembly flexibility when applied to the skin. The skin-safe adhesive layer 808 provides the device assembly with an interface to the skin and separation from the skin and the layers above the skin-safe adhesive layer. It provides a medium for desirable qualities in skin application such as flexibility and breathability.

Similar to previous embodiments, it is understood that some embodiments may not have adhesive on all interfacing surfaces. Skin contact layer 808 may contain adhesive 818 on one side or both sides. The carrier sheet 810 may comprise a coated paper or other suitable material and may be flat or have indentations or raised features in certain locations to accommodate the rest of the device assembly.

Adhesive coatings used in the device assembly may be of any suitable variety and multiple adhesives may be used in the construction of a single CID. A coating may be a combination of different coatings or a non-uniform coating. Any layer may be perforated with holes, slits or other shapes to promote the transmission of moisture and air. This moisture vapor transmission rate (MVTR) is positively impacted by perforations can affect the strength of the adhesive bond to the skin and the durability of CID 800. The perforations may be spaced uniformly, in a pattern, or arranged according to a distribution, or arranged randomly. Perforations may also be applied selectively to areas of each layer. Perforations may be the same on each layer or different. Each layer may independently contain or not contain perforations. The perforation sizes may also be uniform, varying, patterned or sized according to a distribution, which may be random.

Geometric frame 802 provides structure and rigidity to the construct during application of the device and includes adhesive layer to attach the geometric frame 802. The printable layer 804 may comprise visual data tied to the authority (e.g., law enforcement, precinct number, hospital, facility name, EMS, others) that would apply CID 800 to someone in custody. Glucose monitoring inks, and electrically conductive inks may be put on the skin facing layer to monitor biofunctions as well. Depending on the end user's need, layer 820 may comprise glow in the dark inks; inks that are activated or be visible by sunlight, UV light. The colors of the ink may change when activated by sunlight, UV light, sweat, water or other methods. Metallic ink may be used. Other options for ink layer 820 include thermal ink; inks that retain a charge and emit over time, with a light shined on it; inks that change their physical properties with or without particular activation; and inks that change their physical properties with or without particular activation.

To add or enhance frangibility, layer 804 can be designed in a manner wherein it is stiff the ink not flexible so that it pulls apart with some tension. Substrate 804 is strong and stretchable so when stretched the ink breaks apart rendering it optically unreadable and thus not transferable. Preferably, the ink also may be printed in a manner where it stretches a little to allow for movement while still allowing for optical scanning but not at all for pulling.

The adhesive 814 and the substrate 804 must also have the appropriate characteristics to handle moisture either from external sources or that are naturally present on the skin, such as sweat. In some preferred embodiments, there would be a stronger adhesive on the edge meaning the adhesive on the outer layer will have stronger properties than the inner area, keeping the bond of CID 800 stronger at the edges, at the tension areas. This is also a way to reinforce the edges of CID 800 to prevent curling/peeling up.

Printable substrate 804 is suitable for receiving ink in a variety of printing processes, such as sublimation printing, laser printing, xerographic printing, inkjet printing, flexographic impact printing using a ribbon similar to an electromechanical typewriter, or conventional offset or other conventional printing process. It is preferably of low strength and will break apart if subjected to relatively low magnitude mechanical stresses or impacts in any direction. In this application, this characteristic is referred to as frangibility. Insofar as substrate is the base for the applied inventive CID after application, its frangibility makes it substantially impossible to remove, thus adding a measure of security to the device as an identification device. More particularly, frangibility makes it substantially impossible for the device to be moved from one person or thing to another.

Printable substrate layer 804 is preferably perforated and just thick enough to bond to the adhesive and serve as the foundation for dyes and other electronic components described throughout. This will make the substrate frangible so as to prevent intact removal of the substrate or its readable components, thereby preventing transfer to another individual. The substrate must be durable enough to withstand/tolerate printing and preferably impermeable to the dyes printed thereon. Substrate 804 would also be robust enough with proper moisture vapor transmission rates, channeling and other moisture handling properties to prevent any effects from body fluids such as sweat as well as the adhesive to interfere or interact with the data layer applied to the printable layer 804 or the integrity of the entire device 800. In another embodiment substrate layer 808 will have channels on the adhesive layer to allow moisture to escape more readily.

Optically readable layer 803 may comprise data codes as part of the visual display printed layer 804 such as Quick Response (QR), data matrix, bar codes or any other algorithmic code can be read with an optical electronic device can also be added to the construct. These codes will allow an optical electronic reader to pull unique identifiers from the device. These identifiers can be randomly generated codes which when used with a data management system will allow identification, tracking or data manipulation. These codes can serve as a secure form of data communication allowing the reader to pull information from the skin worn device and also communicate back with the device. Given the prevalence of optical visual code readers, the interaction between these codes and the individual can serve any number of purposes for the wearer of the skin device and/or a third party reading the device.

In accordance with a particularly preferred embodiment of the invention, CID 800 is manufactured using glow-in-the-dark Components. This has the advantage of making working in low light situations saves time in emergency situations. CID 800 may be made to glow in the dark by several techniques as described above.

The electronic device 806 may include electronic components i.e., electronically readable, devices such as electrical circuits, processors, resonant, RFID OR Bluetooth devices, UHF (for long distance reading) or NFC, noncontact communication devices, antennas, microchips, printed circuitry, flexible paper batteries, printed battery, sensors or other printed or nano-printed electronics. In some embodiments, the device or sensors are powered by a battery that is charged by the user's body heat or electricity created by the user's body.

Given the prevalence of near field communication and Bluetooth readers, such as smart phones, tablets, watches and the like, the interaction between these technologies and the individual can serve any number of purposes for the wearer of the skin device and/or a third party reading the device. The non-contact communication device could provide constant connection to other Bluetooth compatible components.

Electronic components 806 add a level of security and functionality over optically read codes. These devices can store more information, be reprogrammed, keeping a rolling count of the number of times the device was read and a variable rolling code for authenticity to increase the security of the CID. This functionality creates any number of advantages given the application. The rolling code in addition to counting can also dynamically tailor the information being displayed based on the count or number of times CID 800 is read. For example, on the first read an instructional screen can be provided to educate the user. On the second read the instructional video can be replaced with a highlighted tutorial and on the third read the instructions are replaced with a link to more information. Furthermore, nano-sized components, preferably BLE particles can be added at this stage used to confirm the authenticity of the skin worn device. In another embodiment, a flexible metal sheet would serve as the substrate layer and an RFID OR BLE could be printed thereon. print on the metal itself. In preferable embodiments, the RFID OR BLE would have to have a white layer on it. Data processors such as circuits, microchips and microprocessors can be added to the device in conjunction with a conductive ink to create a skin wearable computer-processing unit.

As discussed above, components can be used to determine whether CID 800 has been tampered with or removed from an individual, whereby when the product is removed it is inoperable. The functionality of the device can also be limited or ceased based on the variables unrelated to the physical state creating a nonphysical frangibility. The device using a combination of electronic components and software can determine when CID 800 has been removed from one person and applied to another. Security components such as holograms may be added in the final step for authentication.

FIG. 15 shows CID 800 being used in system 801 with CID 800 and smart device 803 In a more preferred embodiment, the battery 809 would be a paper battery that runs it for at least 6 hours continuously. CID 800 could be either placed on the deltoid or between the shoulder blades or in another location where these vital signs could be measured. The CID is paired to a smart communication device 821 such as mobile phone, tablet, computer or other device with a wireless communication protocol using technology such as Bluetooth. In preferred embodiments, Bluetooth Low Energy (BLE) compatible devices would be utilized. The smart device 821 would also comprise an optical scanner, and in preferred embodiments, would comprise a camera or other means to take a picture. In an alternative embodiment, the sensors would be physically separate from the CID itself but connected by BLE to the CID. CID 800 would have both local pairing through BLE 820 and similar to the systems described above, smart communication device 803 would have a bi-lateral connections through the Internet 828 to central processor 830 which would include software 832 that would process the readings from the sensor 806 and store them for future retrieval and send an alarm when the vital signs would be headed towards unacceptable levels. In a preferred embodiment, the software on the local smart device would also process the readings from the sensor and store them for future retrieval and send an alarm when the vital signs would be headed towards unacceptable levels. Non-transferability of a device is ensured when physical removal from the wearer's skin impedes its functionality and is deactivated. For example, removal of device may trigger an alarm when a sensor is disengaged adhesive from remaining device or when a sensor is no longer sensing skin contact (e.g., temperature. pH, etc.). There also may be a "grace period" for removal to adjust or clean the area. Additionally or alternatively, the device may be remotely deactivated even if the device is intact and capable of continued function.

In an alternative embodiment (not shown) the CID with one or more physiological sensors with an RFID connection and a battery is used to provide real time physiological data that can be integrated into the system. Such an embodiment would be thin and light weight and allow for both human readable and RF scannable information for the CID as described above. This embodiment can meet the flexibility lightweight requirements by using preformed plastic housings such as thermoformed, vacuum formed to achieve thin wearable and light packaging that when sealed by heat sealing (preferred) or activators, coatings and or glues to properly seal the package. By having a thin package the biometric sensors are very close to the human body and will have better signal quality reducing the complexity of the sensing circuits.

This embodiment allows for firmware in the sensors and/or software in the system to use the real-time biometrics as triggers for alarms and for making the CID device frangible. To improve battery shelf life and provide an on-off switch can be challenging. This embodiment uses the NFC signal to turn on the microcontroller and has the ability to use an RF characteristic to turn off the sensor to preserve battery life. Furthermore, small psychological sensors such as optical, temperature and accelerometers can be added to the micro-controller for the capture of physiological sensors. In a preferred embodiment, for an added layer of security, there would be built in firmware frangibility where all data would be removed from the device, and not allow the device to be used after a set number of hours.

CID 800 would be particularly useful in application relating to taking custody of a person (e.g., a person who has escaped a secure facility or wandered off from a group home). For example, a person may be neurologically impaired and be unwilling or unable to communicate physical distress. In preferred embodiments, CID 800 would be both identify specific, time specific and location specific while providing continuous vital sign monitoring. In preferred embodiments, the sensor readings would be recorded both locally on the local smart device and in the remote database for both security purposes and quick information delivery. In a preferred embodiment, when if the sensor readings indicate concerning vital signs, an alarm/notification would be sent to the officer's smart device, as well as emergency services and the local precinct. Periodically, in response to prompting the system checks data which has been input into the system to determine whether an alarm condition exists. An alarm condition may be also indicated by a complaint which the consumer application downloaded by the user. If an alarm condition is found to exist, the system sends text messages to the smart phone.

In accordance with a preferred embodiment of the invention, information stored is retrievable by individuals providing health care at the facility to provide various services, such as patient badge replacement, blood pressure measurements, body temperature measurements, administration of nutrition and/or drugs, and so forth. Such prompting may be done by any number of means, such as a handheld mobile device sounding an alarm and presenting an on-screen prompt for a particular service to be provided.

The continuously recorded data would be saved to the central server (as described above) in a format that is appropriate for presentation in court with security protocols put in place to ensure that the data (which would include sensor data, time and location of readings) is not alterable after recording. The device would be particularly useful during the critical period of time when a person who may be non-communicative or uncooperative is taken into custody in the field until they arrive at intake at an appropriate facility, such a patch can be used. The lack of communication could be due to a number of factors: non-cooperation, inability to speak and/or understand spoken English, mental illness, neurological disorders or developmental or other disabilities. In an alternative embodiment, CID 800 would be printed in the authorized vehicle with its unique QR code. Duplicate CIDs could be printed at the precinct or other authorized location to continue to monitor vital signs for at risk detainees.

The combination of sensors, a frangible, non-transferable device authenticated with an authorized smart device and software with appropriate security protocols provides a system that provides accurate, unalterable data on time, location and vital signs readings. Even without a verified government identification (such as a driver's license), the ability to take a picture of the person would also be time stamped and can be correlated or triangulated with other information including information from dash cam, body cam and street cameras as well as bystander cameras.

While it could be used in a situation of detainment for authorities such as law enforcement, it is also useful for other first responders. For example, there could be a mass fire, several people are rescued and get the CID 800 applied and then an alert is sent out to the EMTs in case anyone's vital signs are concerning. This is particularly helpful in situations where there are a number of people injured and the traditional triage process is inefficient. In a preferred embodiment, EMS will be alerted immediately if someone's vital signs show possible distress, and a message could be sent via the central server that additional EMS units are needed.

It is also contemplated that CID 800 could be paired to another CID of an authorized user. For example, an authorized user such as medical personnel, having multiple detainees or injured people, would not have to individually pair each CID to a device but would rather have their CID paired to a specific device so that alerts could be sent quickly to the smart device of an authorized user.

Figure 16:
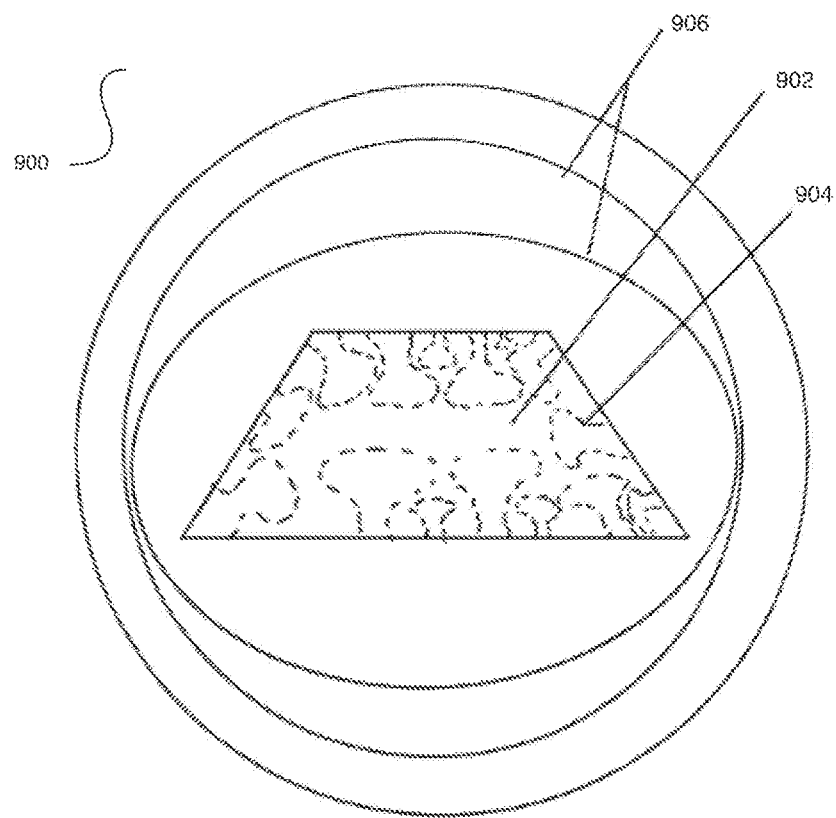
FIG. 16 is a top view an alternative embodiment of a CID.

FIG. 16 shows a top view of a preferred embodiment of the frangible design structure of CID 900 that can be found within the areas of the electronic device that have no components besides a substrate. The dotted lines represent perforations 902 that will tear upon removal. The dotted lines 902 can also represent full die cuts through the substrate. This design has large bobble edges 904 which promotes adhesion to the skin even when the device is being removed regardless of the direction. The large bubbles have a large surface area and therefore a greater adhesion and then taper down. The tapering ultimately leads to tearing of the material and the subsequent antenna 906.

An electrophoretic display may be incorporated into a CID as a means to display information such as patient data or scheduled events. The display may update its information according to the available energy provided by an energy harvesting source, transmitted power, energy storage component, battery, or combination including battery-less systems. The screen refresh rate may be changed dynamically based on energy availability or other factors. Screen refresh may also be temporarily disabled when zero energy consumption is desired. A flexible electrophoretic display may allow incorporation into a skin-applied identification system by allowing the total assembly to conform to the site of physical application where individual identification and security clearance is necessary.

The inventive system can also incorporate biosensors that can measure skin or core temperature changes, heart rate, hydration, UV Exposure, glucose level (using glucose ink or glucose sensor for example) and use the wireless transmitter to send the information to an eternal device or reader. The device's application directly to the skin makes it ideal for physiologic applications. In an alternative embodiment, micro needles are placed on the device in direct contact with the skin. These micro needles will take small samples from the skin which can be used for biologic testing post removal of the device.

Thus, the device could be used to monitor for basic measurements that are relevant in any setting in or outside of healthcare and can be used as an early indication for medical conditions heat exhaustion, hypothermia, sepsis by measuring biometrics such as salt content, foreign compounds and even dehydration. For monitoring emergency situations (for example in a combat or bioterrorism zone) other sensors such as pressure sensors, radiation sensors, chemical weapons sensors, radiologic sensors, paper sensors may be useful. In some embodiments, the CID could monitor skin temperatures changes over time with the probability of developing hypothermia. Conversely, by measuring the changes to core temperature or hydration, the CID can be used as a monitor for heat exhaustion or UV exposure. The data could be saved remotely but not locally. Frangibility of the device is maintained since as the substrate stretched, the circuit breaks and any local data is lost.

In an alternative embodiment the CID can be placed in a visible area such as the hand, forearm, or shoulder and paired to biometric measuring device(s) placed in an area more conducive to accurate measurements. For example, a temperature monitor can be placed under the arm which is not visible. This temperature monitor is connected wirelessly to the visible CID such that when the visible CID is scanned the temperature reading from the nonvisible device is transferred. This allows biometric sensors to be placed in the most effective places for biometric measurements while a CID is more easily accessible for scanning or more appropriately placed for transmitting a signal. When using biometric sensing, the lack-of-physiological sensor data is an indication of the sensor not being worn, or being transferred and both the sensor and the cloud based system can deactivate the sensor and/or provide alarms to the caregiver and system.

In preferred embodiments, the electronics would be encapsulated by an ultrathin layer under 10 mm, preferably 5 mm thick Polyethylene terephthalate glycol, known as PETG or PET-G which is a thermoplastic polyester that delivers significant chemical resistance, durability, and formability for manufacturing. Using thin lightweight Preform Plastic (Thermoform or Vacuum form material) material to encapsulate flexible electronics, provides for a flexible lightweight package that can be affixed to the body with adhesives. This material is lightweight, comfortable, and can allow for longer adhesive wear as the electronics do not present a significant gravity pull. Using transparent polished material allows for LED light and photo-receivers to radiate and absorb the emitted waveforms. This would also simplify the manufacturing process. In preferred embodiments, there may be a lens added for illuminating the skin surface to allow for pulse oximetry readings.

By using a heat sealed process, the enclosures are waterproof and dust proof resulting in less risk and harm to patients and electronics. Additional coatings, glues, and activators (chemicals that react and melts and seals) can enhance functionality. Using thin material allows for close contact of sensors to skin, with better light transmission and thermal transfer. In alternative embodiments, using a dual adhesive backing can allow for easy removal can changing of adhesives while using the same electronic enclosure. This supports the use of less aggressive adhesives of patients for longer wear times saving the user from having to re-attached the electronics into the system.

In a preferred embodiment, the CID comprises encapsulated electronics with a temperature chip as well as an additional optical component to facilitate pulse oximetry readings. The encapsulated electronics are affixed to the adhesives using a low-tack adhesive that is surrounded by a more aggressive adhesive. There are two versions of the more aggressive adhesives to allow for the clinician to determine which adhesive is best suited for the patient.

In preferred embodiments, there is a non-replaceable, non-rechargeable, battery that once activated will allow the CID to take measurements for up to 30 days with a shelf life of 1 year. In preferred embodiments, the CID has the ability to store greater than 4 days' worth of data should the CID not be in communication with an offline device.

In preferred embodiments, the CID comprises a microcontroller has a certified Bluetooth stack. The device uses the NFC protocol to wake up the processor and transmit the serial number of the device to the mobile application The serial number of the device is the Bluetooth MAC (Media Access Control) address. The data is protected and encrypted.

In a hospital setting this is in contrast to prior art systems where hospital wristbands are used which track the band not the patient and can be easily copied (or found discarded in the trash), or bar code systems where staff scan stickers corresponding to the patient and do not need to be physically in front of the patient to perform these activities. Furthermore, an RFID system alone, merely verifies the existence of the band not necessarily the patient. Alternatively, when the patient is outside of the hospital no identification is available and patients use log in and password systems to verify identity outside of the hospital.

In another embodiment, multiple CIDs can communicate with each other wirelessly and transmit information wirelessly. This data can be transferred when any one of the CIDs are scanned or the data can be transmitted wirelessly to any device which can read the receive the signal wirelessly. Receiving device can include gateways, smart devices and smart home devices.

Costs associated with in-hospital (in-patient) care are predictably and substantially more expensive to as compared to care outside a hospital (out-patient care). In addition, care at either a hospital or out-patient facility can be physically challenging, potentially dangerous, and emotionally difficult for many patients. This is particularly true for those who are immune compromised, developmentally disabled, have mobility issues, transportation issues, or limited fiscal resources. During limited hospital capacity and during public health emergencies such as a pandemic, non-urgent procedures may be delayed. As such, it desirable to consider opportunities to provide diagnosis and treatment in the home setting.

In a preferred embodiment, the device and associated system elements may be used to test for and manage Obstructive Sleep Apnea (OSA). OSA affects approximately 20% of all US adults, of whom about 90% are undiagnosed. OSA undiagnosed can shorten life expectancy by several years. A primary reason for the lack of diagnosis is cost, convenience, and comfort of performing associated tests. Currently, there are two methods of testing (1) Polysomnography (PSG) Wired Sleep Laboratory Test and (2) Home Sleep Apnea Test (HST). In the first of these, PSG testing is performed in a sleep laboratory where such can be located either in a hospital or in a standalone facility.

The Sleep Laboratory test is the most complex of OSA testing. Such testing requires the use of a Type 1 monitoring device. This device is required to include a minimum of four channels of EEG; electro-oculogram (EOG), and electromyogram (EMG). All of which are used to determine sleep stage. Additional Type 1 measurements include electrocardiogram (ECG), airflow, respiratory effort, body position and oxygen saturation. A sleep technician (attended) is typically physically present. Laboratory sleep testing can also be performed using a Type II sleep testing device. This device is similar to the Type I device but without the need for direct technician supervision (unattended).

Home Sleep Apnea Tests (HST) are performed in the home environment. Present prior art systems use a Type III sleep testing device. Such devices typically monitor a minimum of four channels that include one or more channels of respiratory effort, airflow, oxygen saturation, and heart rate/ECG. These systems typically use a simplified breathing monitors that track the patient's breathing, oxygen levels, and breathing effort while worn.

Devices used to support Home Sleep Apnea (HST) studies divide into three categories: (1) limited vital sign wearables, (2) finger attached Oxygen ($O_2$) saturation measurement devices (commonly known as PulseOx devices), and (3) finger and wrist attached multisensory measurement devices. Wearable vital sign measurement devices, such as a vital sign ring, are limited in that such only capture a minimal amount of required sleep apnea related parameters. Therefore, such devices provide insufficient data to determine tidal airflow and sleep time profile. As such, these devices do not meet the criteria of a Medicare defined Type III or Type IV HST device. The finger attached $O_2$ saturation based devices capture $O_2$ saturation information from which heart rate and blood oxygen levels can be determined. However, this limited amount of data is not sufficient to generate a sleep profile or determine tidal airflow. Finger and wrist attached multisensory measurement devices can meet the requirements of a Type III medical device, but the overall system does not capture tidal airflow nor generate a Sleep Time profile.

In a preferred embodiment, the CID system is specifically designed to meet the Medicare requirements of a Type IV sleep apnea medical device. The use of a supplemental tidal airflow device and the supporting of an associated algorithm designed to provide sleep time profile, provides a more comprehensive set of data on which to base a sleep apnea remedial action recommendation. The mechanical design of the flexible, low profile of the CID physical package allows for greater comfort and a sleep pattern more representative of their normal sleep profile therefore generating a superior data based upon which to make remedial recommendations. The preference for such a combination of attributes is reflected in Medicare's presently providing for the highest level of reimbursement for such system.

A preferred embodiment of system and related algorithms uniquely provides Type IV device test results and sleep profile. Type IV results provide for a far more accurate basis for prescribing OSA remedial actions. If remedial actions include surgical implanting of a stimulation device, the CID and system can also be used post-surgery to monitor for the effectiveness of the implant action. For example, a sleep apnea remediation plan may involve (1) implant placement in the upper chest area, (2) Bluetooth connection between the implant and the third party control unit (typically placed at the bedside), and (3) periodic adjustment of the stimulation rate. Such a stimulation device could be used in combination with the present CID system to "monitor and facilitate communication between the patient and their sleep apnea physician to adjust stimulation settings. For example, if the CID was attached to the patient and the vital signs of heart rate, respiration rate, and $O_2$ saturation were monitored, a sleep profile could be continually generated. The system would then compare the measured sleep profile versus a sleep physician recommended profile and send the physician an alert when there was an "out of range" event detected. The doctor could then use the CID system to communicate to the patient that they need to manually adjust the sleep apnea management settings. The CID system could simply post such a message on a bedside display or, depending on severity of the condition, send an alert to a cell phone or some other more urgent alert means. This real time monitoring of the patient's response to the function of the stimulation device allows for adjustment and undue side effects. In an alternative embodiment, based on pre-set physiologic parameters, there may an automatic alert sent to the patient to adjust their device or an automatic shut off with an alarm, that alerts the user to call their physician. In another alternative embodiment, the sensor data will manage in real time the function of the stimulation device based on real-time physiologic sensing of appropriate parameters that would indicate that sleep apnea is evolving or in progress so as to deliver the appropriate amount of stimulation needed to manage sleep. The small cross-sectional area and minimal thickness allows the CID to be worn by the patient with a high degree of comfort and therefore capture a more representative indication of the true patient sleep pattern.

The combination of the non-transferable CID married to a central system, means that any data, information and measurements taken are updated in local and central databases. The central server can send notices (alarms, notices, follow up reminders and check-ins and the like), thus putting in a process in place to keep the wearer (and/or their designated caregiver) well apprised of any vital information that may need to be communicated.

When the CID is paired with a smart phone and scanned, the geolocation is determined and there may be messages or alerts sent to the phone to remind the user that they are near their pharmacy to pick up a prescription, or near the cleaners to pick up their dry cleaning or they may opt into promotional offers where they may receive special offers in the area from preferred vendors.

The advantages of an integrated system with a non-transferable cutaneous identification device which accurately identifies and verifies their location becomes acutely evident during situations where tracking and tracing are a must. During an outbreak, epidemic or pandemic, in addition to secure identification, tracking and contract tracing becomes a high priority to mitigate the spread of disease. This system enables accurate location tracking, contact tracing and, in preferred embodiments with Bluetooth sensors all the time. By having a system track CID wearers' locations and potential interactions with others, given their geolocations, make notifications more efficient and accurate. This is vastly improved from a smartphone system without a CID. This pairing of the CID with the smartphone means that the locations can be accurately traced. By having the CID scanned at various locations (stores, doctor's office, work, gym, etc.), there is a record of time and location and also proximity to others.

Additionally, with an option to measure biometrics through other paired devices, it is possible to have a wearer's symptoms tracked over time. There could also be a requirement to self-report symptoms in the app twice a day. The CID can comprise sensors that measure biometrics—such as body temperature. As discussed above, other sensors can be added that can detect or measure for heat exhaustion, hypothermia, sepsis by measuring biometrics such as salt content, foreign compounds and even dehydration UV exposure, skin temperatures changes over time, glucose, salt content, blood alcohol level or detect the presence of other substances. Such measurements and tracking can be particularly to medical professionals in determining diagnosis and treatment plans in an urgent situation.

The system can also send alerts to someone to be aware of their systems and go to the hospital if they have certain other symptoms, making the system function as individual specific care as opposed to a generic blast. Outside of a pandemic, the tracking and tracing functions are particularly helpful to support public health in general to be aware of smaller outbreaks and to send out alerts, so people are acutely aware of their symptoms. In a preferred embodiment, there would be self-reporting of behavior (handwashing, gargling) and tracking of the same to see how timely information can shape individual behavior and public health outcomes.

The versatility and functionality make the CID an ideal virtual wallet with both identification and payment options. Depending on the user's pre-authorizations, the CID can link to an Apple pay type option, function as a room key, etc. . . . . As the CID is secure and not transferable, the usual security concerns are virtually eliminated. This would be particularly useful for ticketed events, invite only events and level access events.

For air travel, in preferred embodiments, this system would be particularly helpful providing added layer of protection because unlike present day boarding passes, the system would use facial recognition software without the annoying need to produce one's license or passport again.

The CIDs may also be manufactured and/or customized at the point of service using in combination with an image capturing device in combination with a thermal transfer printer. This image contains visually readable information for the purposes of identification, and also may contain barcode and data matrix technology for optical scanning and non-contact data transfer technology that will allow specific data to be transferred to a smart device. The process results in a mobile clearer image which includes a photo of the face, visible on all skin tones, with a higher resolution. The tamper proof construct results in a secure, authenticated, nontransferable form of skin worn identification with integrated non-contact connectivity sensors and mobile location services suitable for any number of applications where identification or security is a factor. This mobility allows for the applications in mobile situations where the application of the device can be done in any environment or time sensitive environments where mobile, accurate secure identification is necessary.

For hotels, at check in, instead of a room key, the authorized guests, can get their own authenticated CID which could be used as a room key and also as a means to charge the room. For younger guests who need less freedom, there could be spending/venue limits assigned to the CID and also deactivation or alarms set if one is not in their room by a parent set curfew. This system would also work well with dorm rooms particularly at boarding schools and school trips to tournaments.

For Scout camping, the combination of secure ID, integrated access to medical information and tracking capability are particularly advantageous. Oftentimes, the Scouts are young and when under stress are unable to communicate accurate information. Furthermore, when multiple troops share the same space, it would be easy to quickly identify the Scout and get them the proper medical attention needed. The CID is waterproof and very secure, as it is not transferable.

At hotels, amusement parks, museums, data could be gathered to determine foot traffic to optimize commercial opportunities to plan for appropriate staffing at peak times and when needed maintain social distance and reduced capacity guidelines.

In an institutional seating such as a college, high school, or other campus setting, the electronic component functionality and geolocation capabilities, allows for real-time management and adjustment for capacity, social distancing management and even staffing placement. The real time measurement of biometric factors ensures that those who need may need to testing or other intervention. This device would allow for a more accurate test and stay system that could allow for institutions to stay open and avoid unnecessary shutdowns.

The design may be designed to include aesthetically pleasing enhancements, as it relates to the event. For example, at a baseball game, the user can request their favorite team logo and colors to be printed on the CID to enhance the experience.

The parents or caregivers of both disabled children and adults, particularly those with limited communication skills, will also find the system useful in that it can track the user in designated locations and with the addition of a QR or other scannable code, anyone with a smart phone could scan the code which would send an alert to the appropriate parties to find them in case they are lost.

The background check, security, could connect to multiple global security databases and also could help authorities track down persons of interest quickly, while providing a distinct advantage over fingerprints because easier to execute. The combination of a definitive non-transferable identity combined with technology to track if a person who has checked in has left or is still at the venue. For hotels, amusement parks, festivals, events and the like, digital check points or pillars can be placed in key areas to actively measure attendee flow and location without the use of a batter The inventive system is also useful during lockdown procedures to safely identify who has checked in or out and who is also inside or babysitting or other caregiver services, as well as particularly where staffing is not always consistent, the CID provides a secure mechanism to track who is with the client at what time. For party facilities (e.g., Chuck E Cheese, Jump On In), this is particularly useful when managing a room full of children. For school tour groups, it would provide chaperones an easy way to account for children to be sure that the bus leaves no one behind and everyone is where they are supposed to be.

At amusement parks, the authenticated CID can serve as an admission ticket for up to two weeks. The turnstiles can be fitted with RFID readers, or a person can scan the QR code. The CID serves as a link to identity, park ticket, ride reservation, hotel key and debit card within the resort. In contrast to present systems, such as Disney's Magic Band system, there is no chance of the identifier being lost or stolen. It is well known that Magic Bands are often lost, and much valuable park time is lost by deactivating the band and activating a new band. As the identity is tied to the person, even within a family, there can be different spending limits sets and functionalities granted for each identity.

While illustrative embodiments of the invention have been described, it is noted that various modifications will be apparent to those of ordinary skill in the art in view of the above description and drawings. Such modifications are within the scope of the invention which is limited and defined only by the following claims.

What is claimed:

1. A system for identifying and monitoring at least one vital sign of an individual and providing for the retrieval of information relating to said individual by a plurality of authorized users comprising:
   a. a skin wearable, waterproof, non-transferable frangible individual identification device comprising
      i. a substrate with (i) a top side, and (ii) a bottom side; wherein an adhesive is disposed on the bottom side for adhering the substrate to said individual;
      ii. a marking arranged on the substrate to provide optically scannable information related to said individual wherein the marking can be used for identification, interaction, information exchange, and instructions;
      iii. an electronic device having wireless communication capability with the ability to send, receive, and store information, wherein said electronic device comprises at least one sensor for taking vital sign data;
      wherein once applied to skin of the individual, any tampering with said individual identification device renders the individual identification device inoperable within said system, wherein the marking, the substrate, and the adhesive are biocompatible;
   b. a plurality of receivers;
   c. a computer interface device receiving information from said individual identification device and from said receivers respecting the individual identified by said individual identification device;
   d. a computer system coupled to said computer interface device, said computer system including a memory with an algorithm for processing information collected by said computer system; and
   e. a plurality of authorized computing devices; each authorized computing device comprising a separate set of receivers and a separate service rendering system, each output information from their respective receivers to a common database, the contents of said common database being coupled to the authorized computing device which communicates information to and from a central server.

2. The system according to claim 1, said individual identification device serving as a secure authenticated conduit for gathering and tracking information about the individual wherein when a signal from the individual identification device is received by one of the receivers, said receiver is paired with the individual identification device through wireless communication wherein
   a. data from the individual identification device including data from said sensor and location is periodically sent to the central server and data points are sent and received through secure channels;
   b. alerts are sent based on data collected and processed through the central server; and
   c. utilizes geo fencing or wayfinding technology to determine location.

3. The system according to claim 2, wherein the at least one sensor for taking vital sign data comprises sensors that measure temperature, pulse oximetry and heart rate, and wherein said alerts are sent to authorized device when said sensors detects irregular data.

4. The system according to claim 1 wherein the electronic communication device:
   a. allows for location data collection;
   b. allows for real time passive location tracking; and
   c. allows for data blending and triangulation to estimate location.

5. The system according to claim 1 wherein at least one receiver comprises a camera, photo processing software, and means for a network connection.

6. The system according claim 1, where the individual identification device comprises a noncontact communication device which is
   a. machine readable;
   b. a construct located across multiple layers of the individual identification device;
   c. tamperproof;
   d. comprises a circuit that is rendered inoperable when removed; and e. comprises an insulation layer to boost signal over water-based application like the human body.

7. The system according to claim 1, wherein the system can send first responders the individual's geolocation, and medical information.

8. The system according to claim 1, wherein the individual identification device comprises components that can be powered with energy from one of more the following energy sources from the group consisting of battery, ambient light, solar, static, friction, motion/kinetic, UV, body temperature, heat radiating off the body, LED embedded in adhesive, powered by the surface of the skin, flexible paper batteries, gravity, solar, harvest energy from the body, printed battery, MRI compatible metal batteries.

9. The system according to claim 1, wherein the individual identification device is thermally powered with energy from one of more the following energy sources from the group consisting of battery, ambient light, solar, static, friction, motion/kinetic, UV, body temperature, heat radiating off the body, and LED embedded in the adhesive.

10. The system according to claim 1, said at least one sensor for taking vital sign data can detect or measure for one more of the following parameters from the group consisting of heat exhaustion, hypothermia, or sepsis by measuring dehydration, UV exposure, skin temperatures changes over time, glucose, salt content, blood alcohol level and detecting the presence of other substances.

11. The system according to claim 10, wherein the individual identification device further comprises sensors that can detect removal or can detect a problem with the device, and wherein the system will alert the authorized user and remotely deactivate.

12. The system according to claim 11 some or all of the data is saved when the individual identification device is removed.

13. The system according to claim 1 wherein the individual identification device can directly communicate with other individual identification devices within close proximity to each other.

14. The system according to claim 1 wherein the individual identification device can directly communicate with an external sensor that is not physically connected to the individual identification device, wherein the external sensor and the individual identification device are within close proximity to each other.

15. The system according to claim 1, wherein the individual identification device further comprises sensors that can detect removal of the individual identification device from the individual or can detect a problem with the device, wherein the system will remotely deactivate.

16. The system according to claim 1, wherein the functionality of the individual identification device can be limited or ceased remotely based on the variables unrelated to the physical state.

17. The system according to claim 1, comprising at least one biometric sensor wherein the system will remotely deactivate the individual identification device if the biometric sensor is inoperable.

18. The system according to claim 1, wherein the individual identification device would have a diameter less than about 50 mm, with a thickness less than about 3.3 mm.

19. The system according to claim 18, wherein the individual identification device weighs under about 4 grams.

20. The system according to claim 1, wherein the individual identification device would have a diameter of about 22 mm to about 50mm, with a thickness of 3.2 mm to about 5 mm and weigh under 4 grams.

21. The system according to claim 1, wherein the individual identification device further comprises a battery that lasts for 30 days use.

22. The system according to claim 1 wherein the marking comprises ink.

23. The system according to claim 1 wherein the marking comprises embossing.

24. The system according to claim 1 wherein the marking comprises engraving.

25. The system according to claim 1 wherein the system will send the central server an alarm if a sensor does not send data at prescribed intervals.

* * * * *